(12) United States Patent
Dikeman

(10) Patent No.: US 11,541,174 B2
(45) Date of Patent: Jan. 3, 2023

(54) CLINICAL ASSESSMENT OF AN INTRAVENOUS CATHETER SITE

(71) Applicant: Nexus Medical, LLC, Lenexa, KS (US)

(72) Inventor: W. Cary Dikeman, Lenexa, KS (US)

(73) Assignee: Nexus Medical, LLC, Lenexa, KS (US)

( * ) Notice: Subject to any disclaimer, the term of this patent is extended or adjusted under 35 U.S.C. 154(b) by 837 days.

(21) Appl. No.: 16/516,969

(22) Filed: Jul. 19, 2019

(65) Prior Publication Data

US 2021/0016065 A1 Jan. 21, 2021

Related U.S. Application Data

(63) Continuation of application No. 16/516,828, filed on Jul. 19, 2019, now Pat. No. 11,400,212.

(51) Int. Cl.
*G06K 9/00* (2022.01)
*A61M 5/168* (2006.01)
(Continued)

(52) U.S. Cl.
CPC ........ *A61M 5/16836* (2013.01); *A61M 25/04* (2013.01); *A61M 25/0606* (2013.01); *G06T 7/0014* (2013.01); *G06T 7/80* (2017.01); *G16H 10/60* (2018.01); *H04N 5/232945* (2018.08); *A61B 5/0077* (2013.01); *A61M 25/02* (2013.01);
(Continued)

(58) Field of Classification Search
CPC .............. A61M 5/16836; A61M 25/04; A61M 25/0606; A61M 25/02; A61M 2005/16863; A61M 2205/3306; A61M 2205/52; A61M 2205/583; A61M 2205/6072; A61M 2209/02; A61M 2005/14288; A61M 2205/3561; G06T 7/0014; G06T 7/80; G06T 2207/30021; G16H 10/60; G16H 30/20; G16H 40/40; G16H 20/17; G16H 30/40; G16H 40/20; G16H 40/67; G16H 50/30; G16H 50/50; H04N 5/232945; H04N 17/002; A61B 5/0077

See application file for complete search history.

(56) References Cited

U.S. PATENT DOCUMENTS 8,083,524 B2 * 12/2011 Grund-Pedersen .... G09B 23/28
434/262
9,744,344 B1 * 8/2017 Devgon ............... A61B 8/0841
(Continued)

OTHER PUBLICATIONS

Steere, Lee et al.; Reaching One Peripheral Intravenous Catheter (PIVC) Per Patient Visit with Lean Multimodal Strategy: the PIV5Rights Bundle; The Journal of the Association for Vascular Access; Jul. 16, 2019; pp. 31-43; vol. 24, No. 3.
(Continued)

*Primary Examiner* — Shervin K Nakhjavan
(74) *Attorney, Agent, or Firm* — Erise IP, P.A.

(57) ABSTRACT

A system and method for assessing an intravenous catheter site is described in embodiments herein. An application accessible on a mobile device may be used to take calibrated photographs of an intravenous catheter site. The resulting calibrated image may be compared to previously taken calibrated images to determine a complication. Success of treatments to the complication may be tracked and the patient's electronic medical record may be updated.

20 Claims, 38 Drawing Sheets

(51) Int. Cl.
G06T 7/80 (2017.01)
G06T 7/00 (2017.01)
H04N 5/232 (2006.01)
G16H 10/60 (2018.01)
A61M 25/04 (2006.01)
A61M 25/06 (2006.01)
A61M 25/02 (2006.01)
G16H 30/20 (2018.01)
A61B 5/00 (2006.01)
G16H 40/40 (2018.01)

(52) U.S. Cl.
CPC .............. A61M 2005/16863 (2013.01); A61M 2205/3306 (2013.01); A61M 2205/52 (2013.01); A61M 2205/583 (2013.01); A61M 2205/6072 (2013.01); A61M 2209/02 (2013.01); G06T 2207/30021 (2013.01); G16H 30/20 (2018.01); G16H 40/40 (2018.01)

(56) References Cited

U.S. PATENT DOCUMENTS

| | | | | | |
|---|---|---|---|---|---|
| 9,875,339 | B2* | 1/2018 | Namer Yelin | ......... | G16H 50/50 |
| 10,719,980 | B2* | 7/2020 | Mollus | .................. | G16H 50/50 |
| 11,031,136 | B2* | 6/2021 | Grass | ..................... | G16H 50/50 |
| 11,120,893 | B2* | 9/2021 | Choi | ..................... | G16C 20/30 |
| 11,160,489 | B2* | 11/2021 | Rogers | ................. | A61B 5/4836 |
| 2006/0008786 | A1* | 1/2006 | Feygin | ................. | G09B 23/285 |
| | | | | | 434/262 |
| 2012/0190976 | A1* | 7/2012 | Kleinstreuer | .......... | A61B 34/70 |
| | | | | | 604/247 |
| 2017/0032097 | A1* | 2/2017 | Itu | .......................... | G16H 50/50 |
| 2018/0116725 | A1* | 5/2018 | Ashikaga | ............. | A61B 5/7275 |
| 2019/0110767 | A1* | 4/2019 | Nishioka | ............. | A61B 6/5288 |
| 2021/0073978 | A1* | 3/2021 | Schmitt | ................... | A61B 6/032 |
| 2021/0321888 | A1* | 10/2021 | Morris | .................. | A61B 34/10 |

OTHER PUBLICATIONS

Rothlisberger, Dieter; If Euhydric and Isotonic Do Not Work, What Are Acceptable pH and Osmolality for Parenteral Drug Dosage Forms? Journal of Pharmaceutical Sciences 106 (2017) 446-456; www.jpharmsci.org Nov. 2016; F. Hoffmann—La Roche Ltd., Pharmaceutical Development and Supplies, Pharma Technical Development Biologies EU, Basel, Switzerland.

Gagne, Paul et al.; Relationship of Common Vascular Anatomy to Cannulated Catheters; International Journal of Vascular Medicine; Dec. 19, 2017; pp. 1-7; vol. 2017; Article ID 5157914.

Foor, John S. et al.; The Role of the Hemodilution Ratio in Correlation to Blood Flow Velocity and the Impact of Venous Valves in Retrograde Blood Reflux; Presented at the Association for Vascular Access Annual Scientific Meeting; pp. 1-2; Oct. 2019.

Moureau, Nancy; How to Become Flow Righteous: The 1-2-3 Elements of Success; Presented at the Association for Vascular Access Annual Scientific Meeting; pp. 1-4; Oct. 2020.

* cited by examiner

HOSPITAL PIVC ASSESSMENT — 3:27 PM

NEW PIVC 2/7

CLINICIAN WHO PLACED CATHETER
- UNKNOWN
- NURSE
- ICU NURSE
- ER NURSE
- DOCTOR

INSERTED IN UNIT
- UNKNOWN
- MEDICAL FLOOR 5
- EMERGENCY DEPARTMENT
- OPERATING ROOM
- ICU/CCU

ULTRASOUND PLACEMENT
☑ YES ☐ NO

COMMENTS
REDNESS

[BACK] [SAVE RECORD FOR LATER] [NEXT]

HOSPITAL  PIVC ASSESSMENT

NEW PIVC 4/7

SKIN PREP USED

| UNKNOWN |
| --- |
| ALCOHOL PREP PAD |
| CHLORAPREP SEPP™ |
| CHLORAPREP FREPP™ |
| CHLORAPREP 1ML |

IV KIT USED?   — 1104
☑ YES  ☐ NO

COMMENTS
NEW KIT   — 1106

BACK          NEXT

FIG. 11

HOSPITAL PIVC ASSESSMENT

NEW PIVC 5/7 — 1202

IV DRESSING TYPE

- ☑ 3M TEGADERM™
- ☐ 3M TEGADERM™ IV ADVANCED SECUREMENT DRESSING
- ☐ CHLORADERM™
- ☐ SORBAVIEW™ 2000
- ☐ SURESITE™
- ☐ TAPE ONLY
- ☐ NO DRESSING
- ☐ OTHER [          ]

BACK    NEXT

HOSPITAL  PIVC ASSESSMENT

NEW PIVC 6/7 — 1302

PIVC & IV SET SECUREMENT
☐ SUTURELESS SECUREMENT DEVICE
☐ STERILE TAPE STRIPS AROUND PIVC
☑ NON-STERLIE TAPE AROUND PIVC
☐ IV EXT. SET SECUREMENT DEVICE
☐ SPLINT / BANDAGE / TUBULAR NET
☐ SITE DRESS ONLY
☐ NO SECUREMENT
☐ OTHER _____

IV NEEDLELESS CONNECTOR — 1304
☐ IV EXT. SET
☐ NEEDLELESS CONNECTOR
☑ IV EXT. SET + NEEDLELESS CONNECTOR
☐ IV DEAD END CAP
☐ DIRECT CONNECTION TO IV SET
☐ NONE
☐ OTHER _____

NEEDLELESS CONNECTOR BRAND — 1306
☑ NEXUS TKO - 6P  ☐ CLAVE  ☐ MICRO CLAVE  ☐ NONE  ☐ OTHER _____

[BACK]  [NEXT]

FIG. 13

HOSPITAL PIVC ASSESSMENT

NEW PIVC 7/7

HUB / PORT DISINFECTION
☐ ALCOHOL PREP PAD
☑ PREVANTICS PREP PAD
☐ CUROS™ (GREEN CAP)
☐ SWABCAP™ (ORANGE CAP)
☐ SITESCRUB™
☐ DUALCAP™ (BLUE/PINK CAP)
☐ PREVANTICS™ DEVICE SWAB
☐ NONE
☐ OTHER

BACK   NEXT

FIG. 14

HOSPITAL PIVC ASSESSMENT  3:29 PM

PATIENT INFORMATION

ID: 000123
LOCATION: ROOM 503 - BED A
AGE: 45
ADMITTED: 2016-08-03 14:56:27
DIAGNOSIS: GALLBLADDER SURGERY
IV FLUIDS:
INTERMITENT DRUGS:
CONTINUOUS/BOLUS:
BCA DRUGS:

LATEST DWELL REFERENCES

IV SITE INFO

INSERTED: 2016-08-03 15:04:44
VEIN: RIGHT HAND - ACC, BASILIC VEIN
GAUGE: 14G
BRAND: BECTON DICKINSON
DRESSING: 3M TEGADERM™
SECUREMENT: SUTURELESS SECUREMENT DEVICE
NEEDLELESS CONN.:IV EXT.SET
NEEDLELESS CONN.BRAND: NEXUS TKO-6P

COMPLICATIONS

DRESSING:
REDNESS:
SWELLING:
HARDNESS:
PURULENCE:
STREAKING:
HARD VEIN CORD:
LEAKING PIVC:
BLOOD IN CATH HUB:
EXTRAVASTION:

[NEW PIVC LOCATION] DISCONTINUES PREV DWELL

[ASSESS SITE]

[PATIENT DISCHARGED] DISCONTINUES PREV DWELL

[DONE]

HOSPITAL PIVC ASSESSMENT 4:18 PM

PHLEBITIS OBSERVATION — 2804
PHLEBITIS SCALE
PHLEBITIS GRADE AND SEVERITY

MAKE A SELECTION

BACK

---

HOSPITAL PIVC ASSESSMENT 4:20 PM — 2802

PHLEBITIS OBSERVATION
PHLEBITIS SCALE
PHLEBITIS GRADE AND SEVERITY:

MAKE A SELECTION

| SITE OBSERVATION | SCORE | STAGE/ACTION |
|---|---|---|
| IV SITE APPEARS HEALTHY | 0 | NO SIGNS OF PHLEBITIS OBSERVE CANNULA |
| ONE OF THE FOLLOWING SIGNS IS EVIDENT:<br>• SLIGHT PAIN NEAR THE IV SITE OR<br>• SLIGHT REDNESS NEAR IV SITE | 1 | POSSIBLY FIRST SIGNS OF PHLEBITIS OBSERVE CANNULA |
| TWO OF THE FOLLOWING ARE EVIDENT<br>• PAIN AT IV SITE<br>• REDNESS | 2 | EARLY STAGE OF PHLEBITIS RESITE CANNULA |
| ALL OF THE FOLLOWING ARE EVIDENT<br>• PAIN ALONG PATH OF CANNULA<br>• REDNESS AROUND SITE<br>• SWELLING | 3 | MEDIUM STAGE OF PHLEBITIS RESITE CANNULA CONSIDER TREATMENT |
| ALL OF THE FOLLOWING ARE EVIDENT AND EXTENSIVE<br>• PAIN ALONG PATH OF CANNULA<br>• REDNESS AROUND SITE<br>• SWELLING<br>• PALPABLE VENOUS CORD | 4 | ADVANCED STAGE OF PHLEBITIS OR THE START OF THROMBAPHLEBITIS RESITE CANNULA CONSIDER TREATMENT |
| ALL OF THE FOLLOWING ARE EVIDENT AND EXTENSIVE<br>• PAIN ALONG PATH OF CANNULA<br>• REDNESS AROUND SITE<br>• SWELLING<br>• PALPABLE VENOUS CORD<br>• PYRODS | 5 | ADVANCED STAGE THROMBAPHLEBITIS INITIATE TREATMENT RESITE CANNULA |

2806 — 2814 — 2812 — 2810 — 2808

BACK          NEXT

HOSPITAL PIVC ASSESSMENT  4:33 PM

DISCONTINUE PIVC
PIVC SITE PHOTO

REASONS (CHECK ALL THAT APPLY)
- ☐ IV DRESSING CONDITION
- ☐ REDNESS
- ☑ SWELLING
- ☐ HARDNESS
- ☐ PAIN
- ☐ PURULENCE / DRAINAGE
- ☐ STREAKING / RED LINE
- ☐ HARD VEIN CARD BEYOND IV
- ☐ LEAKING PIVC
- ☐ BLOOD IN CATH HUB
- ☐ EXTRAVASATION
- ☐ INFILTRATION
- ☐ INABILITY TO FLUSH / OCCLUDED
- ☐ PHLEBITIS
- ☐ OTHER

COMMENTS

DATE DISCONTINUED

| TUE AUG 2 | 30 |
| WED AUG 3 | 31 |
| THU AUG 4 | 32 AM |
| TODAY 4 | 33 PM |
| SAT AUG 6 | 34 |
| SUN AUG 7 | 35 |
| MON AUG 8 | 36 |

NEXT

3:38 PM

HOSPITAL   PIVC ASSESSMENT

IV DRUGS 1/4
IV FLUIDS - MED / SURG / ONC
SEARCH...
NONE
.IVF + KCL 10 mEq/L YES X - 1 999
.IVF + KCL 20 mEq/L YES X - 1 500
.IVF + KCL 30 mEq/L YES X - 1 333 350
.IVF + KCL 40 mEq/L YES X - 1 250 275
.IVF MAINTENANCE YES X - 1 999
.MAINT IVF + ADDITIVES YES X - 1 250
3% SODIUM CHLORIDE YES X _ 1 50 100
ALBUMIN 25% IV YES X X 1 200
ALBUMIN 50% IV YES X X 1 300
OTHER

3100

BACK    NEXT

FIG. 31

HOSPITAL PIVC ASSESSMENT　　　　　　　　　　　　3:35 PM

IV DRUGS 2/4

INTERMITTENT DRUGS

SEARCH...

- NONE
- ABATACEPT X X mg 500 1500 -500 mg / 100mL (5 mg / mL) X -00:20 01:0...
- ABATACEPT 1,000 mg / 100mL (10 mg /mL) X -00:20 01:00 00:30 N/A N/A N...
- ABATACEPT 750 mg /100 mL (7.5mg/mL) X -00:20 01:00 00:30 N/A N/A N/...
- ACETAMINOPHEN X X .mg 500 1000 -1,000 mg / 100mL (10mg /mL) X - 00...
- ACETAMINOPHEN .mg / - mL X -00:10 00:30 00:15 mg/mL 9 10 11
- ACETYLCYSTEINE FIRST DOSE X X mg/kg 140 160 -mg /- mL X -00:30 02:0
- ACETYLCYSTEINE SECOND DOSE X X mg/kg 40 60 -mg /- mL X -03:35 05:00
- ACETYLCYSTEINE THIRD DOSE X X mg/kg 90 110 -mg /- mL X -14:20 18:00
- ACETYLCYSTEINE X X mg/kg 100 3000 -mg /- mL X -00:45 03:00 01:00 mg/mL 1

OTHER

BACK　　　　　　　　　　　　　　　　　　　　　　　　NEXT

HOSPITAL    PIVC ASSESSMENT                                              4:00 PM

IV DRUGS 3/4

CONTINUOUS / BOLUS - NON-ANESTHESIA DRUGS

SEARCH...

- NONE
- ALTEPLASE .PILMONARY EMBOLISM 90 mg / 90 mL (1 mg / mL) X - N/A CONTINUO....
- ALTEPLASE .STROKE 99kg OR LESS - mg / mL X - YES CONTINUOUS mg/h 30 - 81
- ALTEPLASE .STROKE ABOVE 99kg - mg / mL X - YES CONTINUOUS mg/h  80 82 - 81
- ALTEPLASE EKOS 25 mg / 250 mL (0.1 mg /mL ) X - N/A CONTINUOUS mg/h 0.0 -...
- AMINOCAPROIC DRIP 5 GRAM / 250 mL (0.02 mg / mL) 10 GRAM / 500 mL (0...
- AMIODARONE DRIP 450 mg / 250 mL (1.8 mg / mL) X - N/A CONTINUOUS mg/...
- ARGATROBAN 50 mg / 50 mL (1 mg / mL) X - N/A CONTINUOUS mcg/kg/min 0.1...
- BUMETANIDE DRIP 4 mg / 100 mL (0.04 mg / mL) 20 mg /100 (0.2 mg / mL...
- CHROMIUM 150 mg / 350 mL (0.6 mg / mL) X - N/A CONTINUOUS mcg/kg/min 5 10...

OTHER

BACK                                                                      NEXT

HOSPITAL   PIVC ASSESSMENT

IV DRUGS 4/4

PCA DRUGS - MED / SURG / ONC

3100

SEARCH...

NONE
BUPRENORPHINE
FENTANYL
HYDROMORPHONE .STANDARD DOSE
HYDROMORPHONE HIGH DOSE
MEPERIDINE
METHADONE IV
MORPHINE

OTHER

BACK    NEXT

FIG. 34

HOSPITAL   PIVC ASSESSMENT    4:22 PM

SITE ASSESSMENT 9/10

ON A SCALE OF 1 - 5 (5 BEING THE LOWEST) HOW WOULD YOU RATE YOUR IV THERAPY EXPERIENCE?
☑ 1: VERY SATISFIED   ☐ 2: SATISFIED   ☐ 3: OK   ☐ 4: NOT VERY GOOD   ☐ 5: POOR

DID YOUR NURSE COMMUNICATE TO YOU ABOUT THE NEED FOR YOUR IV?
☐ YES   ☑ NO

WERE YOU SATISFIED WITH THE SKILL OF THE INSERTER?
☑ YES   ☐ NO

WAS THE IV PROCEDURE RELATIVELY FREE FROM PAIN?
☐ YES   ☑ NO

[BACK]   [SKIP]   [NEXT]

HOSPITAL PIVC ASSESSMENT

4:35 PM

PATIENT INFORMATION

PATIENT ID: 000123
BED: ROOM 503 - BED A
AGE: 45
GENDER: MALE
DIAGNOSIS: GALLBLADDER SURGERY

REASONS FOR DISCHARGE — 3602

☐ DISCHARGED
☐ DECEASED / EXPIRED
☐ TRANSFER TO OTHER FACILITY
☐ TRANSFER TO OTHER UNIT
☐ OTHER

DATE DISCHARGED — 3604

| TUE AUG 2 | 1 | 31 |
| WED AUG 3 | 2 | 32 |
| THU AUG 4 | 3 | 33 | AM |
| TODAY | 4 | 34 | PM |
| SAT AUG 6 | 5 | 35 |
| SUN AUG 7 | 6 | 36 |
| MON AUG 8 | 7 | 37 |

3600

[BACK]   [DISCHARGE]

FIG. 36

CLINICAL ASSESSMENT OF AN INTRAVENOUS CATHETER SITE

RELATED APPLICATIONS

This non-provisional patent application is a continuation application and claims priority benefit, with regard to all common subject matter, of commonly assigned U.S. patent application Ser. No. 16/516,828, filed Jul. 19, 2019, entitled "CLINICAL ASSESSMENT OF AN INTRAVENOUS CATHERTER SITE," ("the '828 Application"). The '828 Application is hereby incorporated by reference in its entirety into the present application.

BACKGROUND

1. Field

Embodiments of this invention relate to assessment of patients undergoing medical care. More specifically, embodiments of this invention relate to assessment of intravenous catheter (IVC) insertion sites.

2. Related Art

In a typical patient stay at a medical facility, intravenous fluid is provided to a patient through an intravenous catheter (IVC). Too often a patient receives multiple catheters and multiple insertions of a catheter decreasing patient satisfaction and increasing cost. The patient may experience complications related to the IVC site resulting in soreness, color variation, redness, tissue hardening, streaking, or any other symptom indicative of the complication. The initial symptom may begin as a color variation, for example, a light redness. The healthcare provider may overlook the complication and the complication may not be realized in a timely manner. This may result in worsening of the complication before medical staff is aware of the condition. Alternatively, a healthcare provider may change a catheter unnecessarily. These complications and healthcare provider inconsistencies leads to unnecessarily high costs and low patient satisfaction.

Typically, healthcare providers administer drugs at an easily accessible vein starting at the wrists and, when complication occur, moving up the arm. This is a technique that may result in several IVCs and sticks before the medicine is fully administered. This results in high costs and low patient satisfaction and is avoidable utilizing the techniques and vein analysis described in embodiments herein.

What is needed are systems and methods for decreasing the cost associated with intravenous catheters. Utilizing proficient healthcare staff, correct IVC insertion methods, choosing the correct vein and catheter, utilizing the proper supplies and technology, and, in particular, systems and methods for proper review and assessment of the IVC and the IVC site reduces the number of IVCs used during an average patient stay at a medical facility. With all five steps correctly applied, patient satisfaction increases and cost for IVC decreases. Specifically, review and assessment of the IVC site, as described in embodiments herein, provides the healthcare provider with the tools to quickly determine complications, document and report the complications, and diagnose and prescribe successful treatments.

Further, vein analysis and Computational Fluid Dynamic models of veins may be implemented to find a best vein for the IVC. Embodiments of systems and methods described herein may reduce the number of IVCs used per patient per visit thus reducing healthcare cost and increasing patient satisfaction.

SUMMARY

Embodiments of the invention solve the above-mentioned problems by providing a system and method for assessing an intravenous Catheter (IVC) site. In some embodiments, a mobile device running an application is used to take a calibrated photograph of the IVC site. The resulting calibrated image, generated by the calibrated photograph, is compared to previously stored calibrated images to determine if a complication exists. When it is determined that a complication exists, the application may determine and suggest a treatment to the healthcare provider. Further, the calibrated images may be analyzed to track the progress of the IVC site during treatment and evaluate the success of the treatment.

A first embodiment is directed to a method of assessing an intravenous catheter site, the method comprising the steps of locating the intravenous catheter site via a camera and a display on a mobile device, aligning a calibration object viewed via the display with a calibration zone displayed on the display, and storing a calibrated image of the intravenous catheter site when the calibration object is aligned with the calibration zone.

A second embodiment is directed to a method of assessing an intravenous catheter site, the method comprising the steps of locating the intravenous catheter site via a display on a mobile device, aligning an intravenous catheter viewed via the display with a calibration zone displayed on the display, taking a calibrated photograph of the intravenous catheter site resulting in a calibrated image, and storing the calibrated image of the intravenous catheter site when the intravenous catheter is aligned with the calibration zone.

A third embodiment is directed to a system for assessing an intravenous catheter site, the system comprising a camera for capturing a calibrated image of the intravenous catheter site, wherein the calibrated image is calibrated by aligning a calibration object viewed through the camera with a calibration zone projected on the display, one or more non-transitory computer-readable media storing computer-executable instructions that, when executed by a processor, perform a method of assessing the intravenous catheter site, comprising the steps of comparing the calibrated image with at least one previously stored calibrated image of the intravenous catheter site, and determining a difference between the calibrated image and the at least one previously stored calibrated image, wherein the difference is indicative of a complication.

A fourth embodiment directed to one or more non-transitory computer-readable media storing computer-executable instructions that, when executed by a processor, perform a method of determining a blood vessel of a patient for receiving a medication via an intravenous catheter, the method comprising the steps of obtaining blood vessel characteristics, generating a blood vessel model based on the blood vessel characteristics, simulating blood flow in the blood vessel model, simulating an introduction of the medication into the blood vessel model via the intravenous catheter, and determining a medication effect on the blood vessel model.

A fifth embodiment directed to one or more non-transitory computer-readable media storing computer-executable instructions that, when executed by a processor, perform a method of determining a blood vessel of a patient for receiving a medication via an intravenous catheter, the method comprising the steps of, obtaining blood vessel characteristics via ultrasonography, generating a blood vessel model based on the blood vessel characteristics, simulating blood flow in the blood vessel model using computational fluid dynamics, simulating an introduction of the medication into the blood vessel model via the intravenous catheter, and determining a medication effect on the blood vessel model.

A sixth embodiment directed to one or more non-transitory computer-readable media storing computer-executable instructions that, when executed by a processor, perform a method of determining a blood vessel of a patient for receiving a medication via an intravenous catheter, the method comprising the steps of obtaining blood vessel characteristics from a plurality of blood vessels via ultrasonography, generating a plurality of blood vessel models, wherein each of the plurality of blood vessel models corresponds to at least one blood vessel of the plurality of blood vessels, simulating blood flow in each of the blood vessel models using computational fluid dynamics, simulating an introduction of the medication into each of the blood vessel models via the intravenous catheter, and determining a medication effect on each of the blood vessel models.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages will be apparent from the following detailed description of the embodiments and the accompanying drawing figures.

BRIEF DESCRIPTION OF THE DRAWING FIGURES

Embodiments of this disclosure are described in detail below with reference to the attached drawing figures, wherein:

FIG. 5 depicts an embodiment of the application presenting a patient information screen;

FIG. 8 depicts an embodiment of the application presenting an IVC placement screen;

FIG. 10 depicts an embodiment of the application presenting a new IVC vein location screen;

FIG. 11 depicts an embodiment of the application presenting a skin preparation screen;

FIG. 12 depicts an embodiment of the application presenting a dressing screen;

FIG. 13 depicts an embodiment of the application presenting an IVC site dressing screen;

FIG. 14 depicts an embodiment of the application presenting a disinfection screen;

FIG. 15 depicts an embodiment of the application presenting a complete patient summary screen;

Figure 16A:
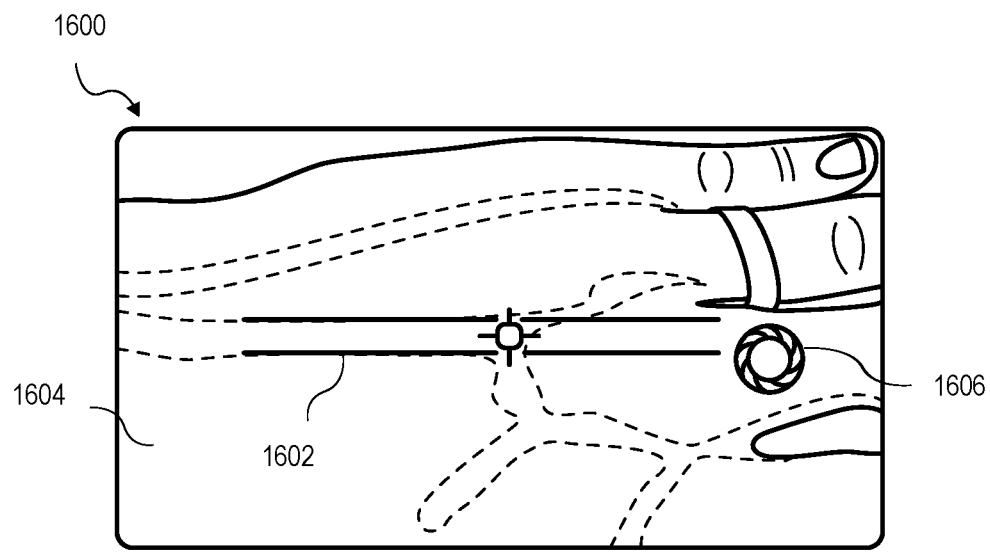
Figure 16B:
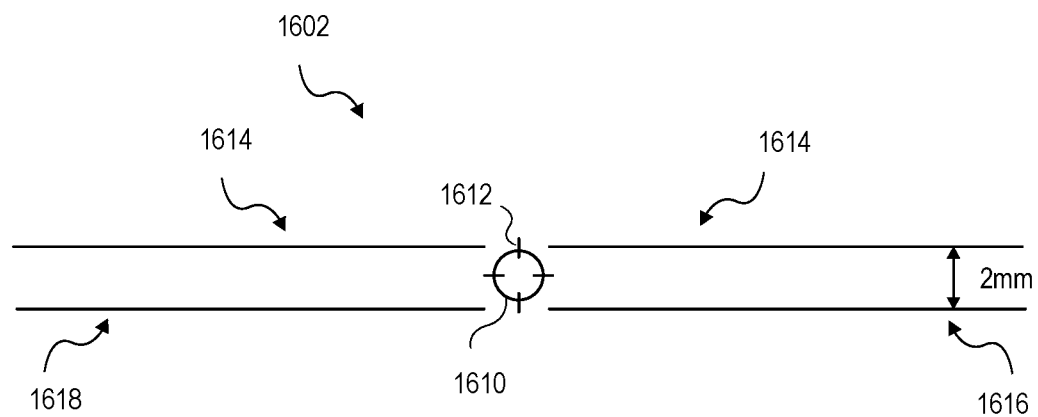
Figure 17:
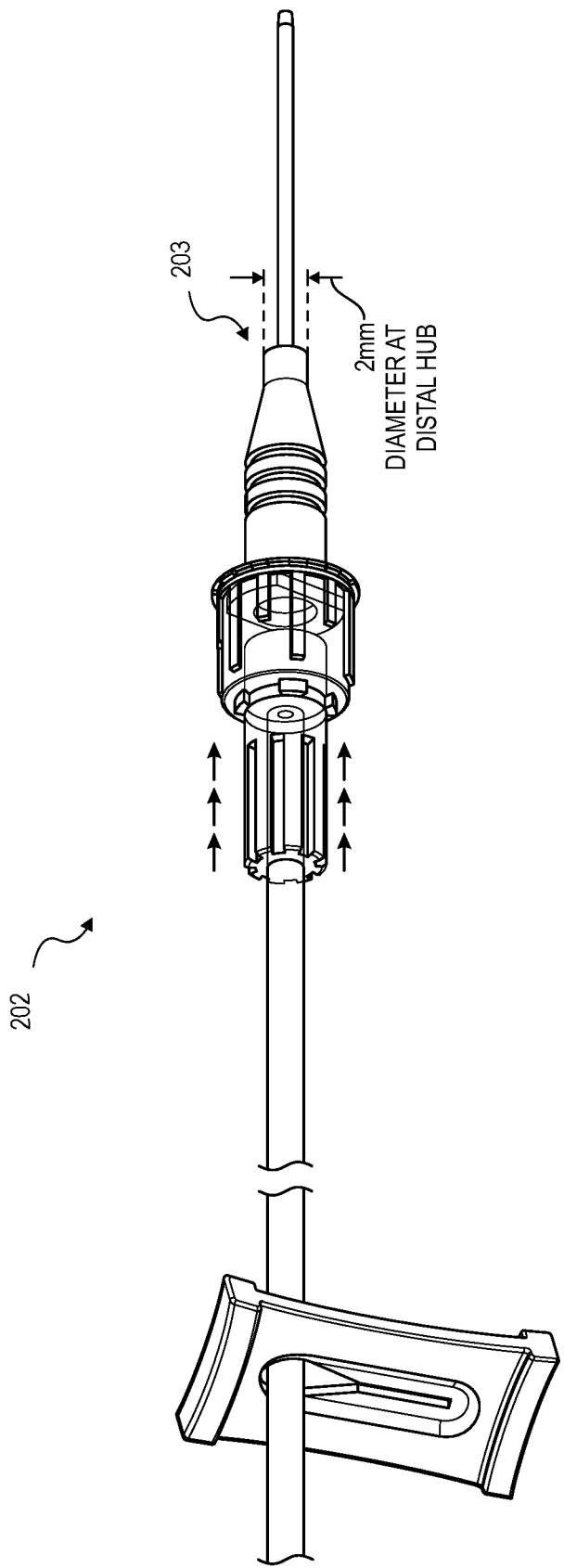
Figure 18:
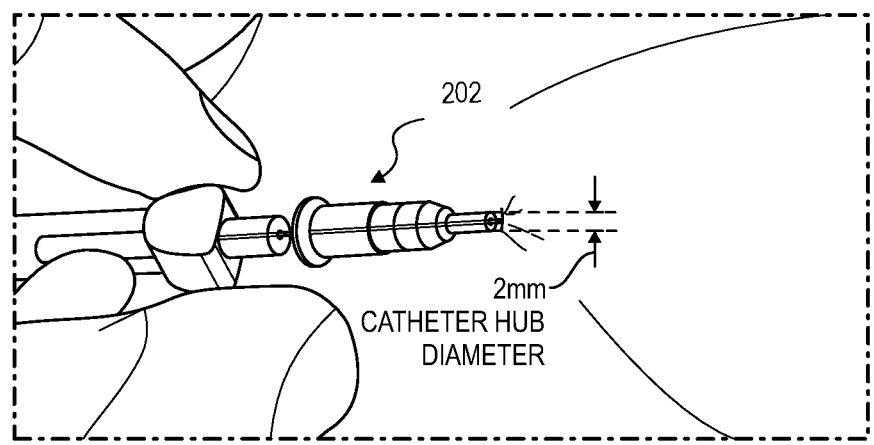
Figure 19:
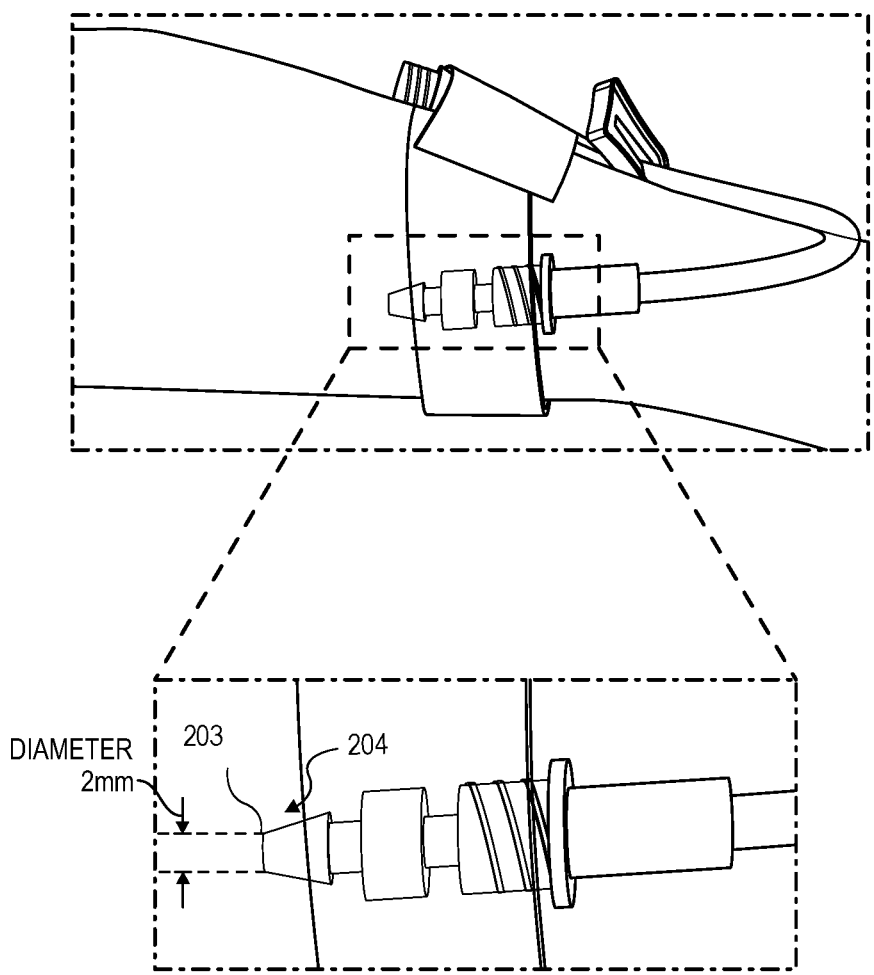
Figure 20:
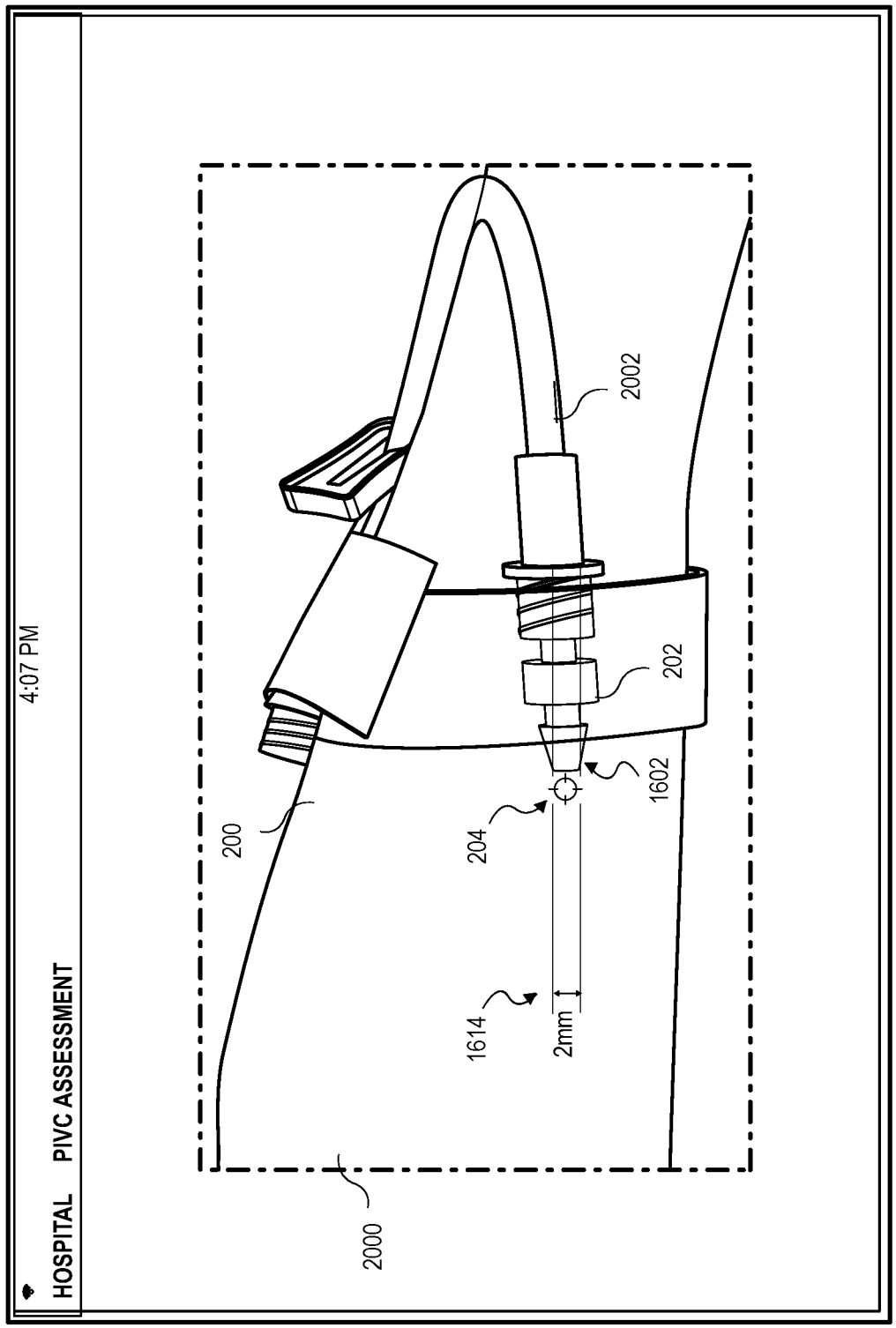
Figure 22:
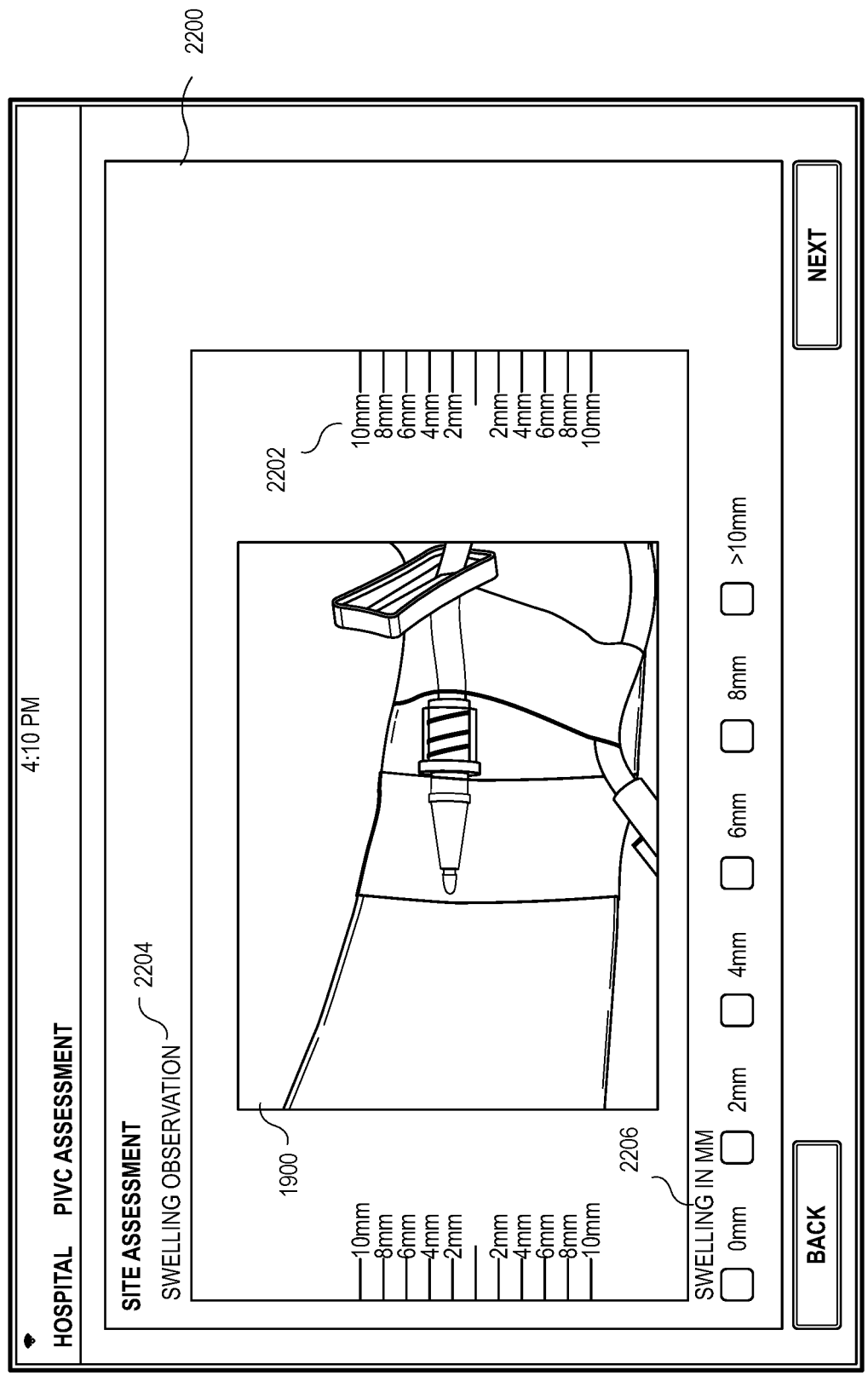
Figure 23:
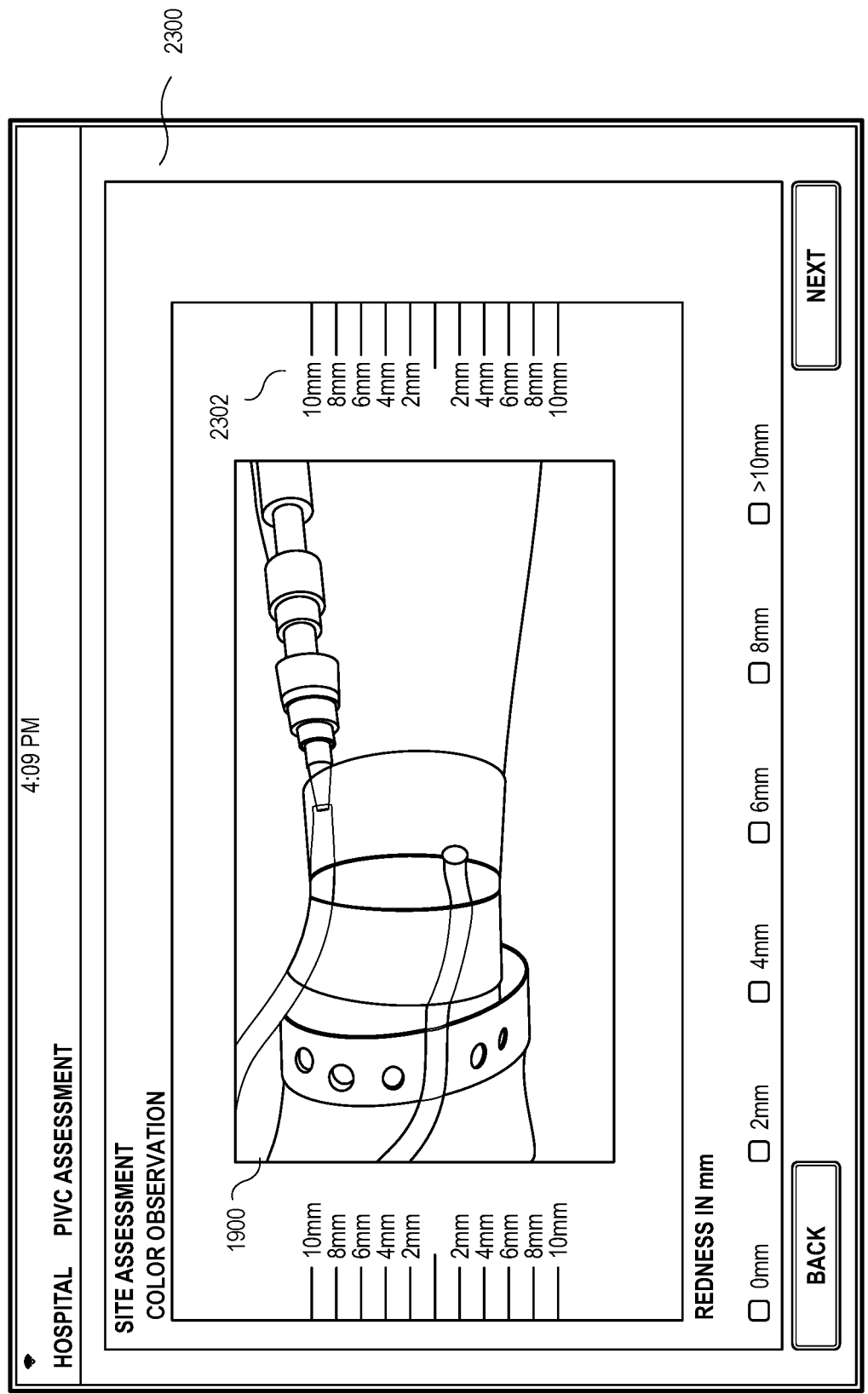
Figure 24:
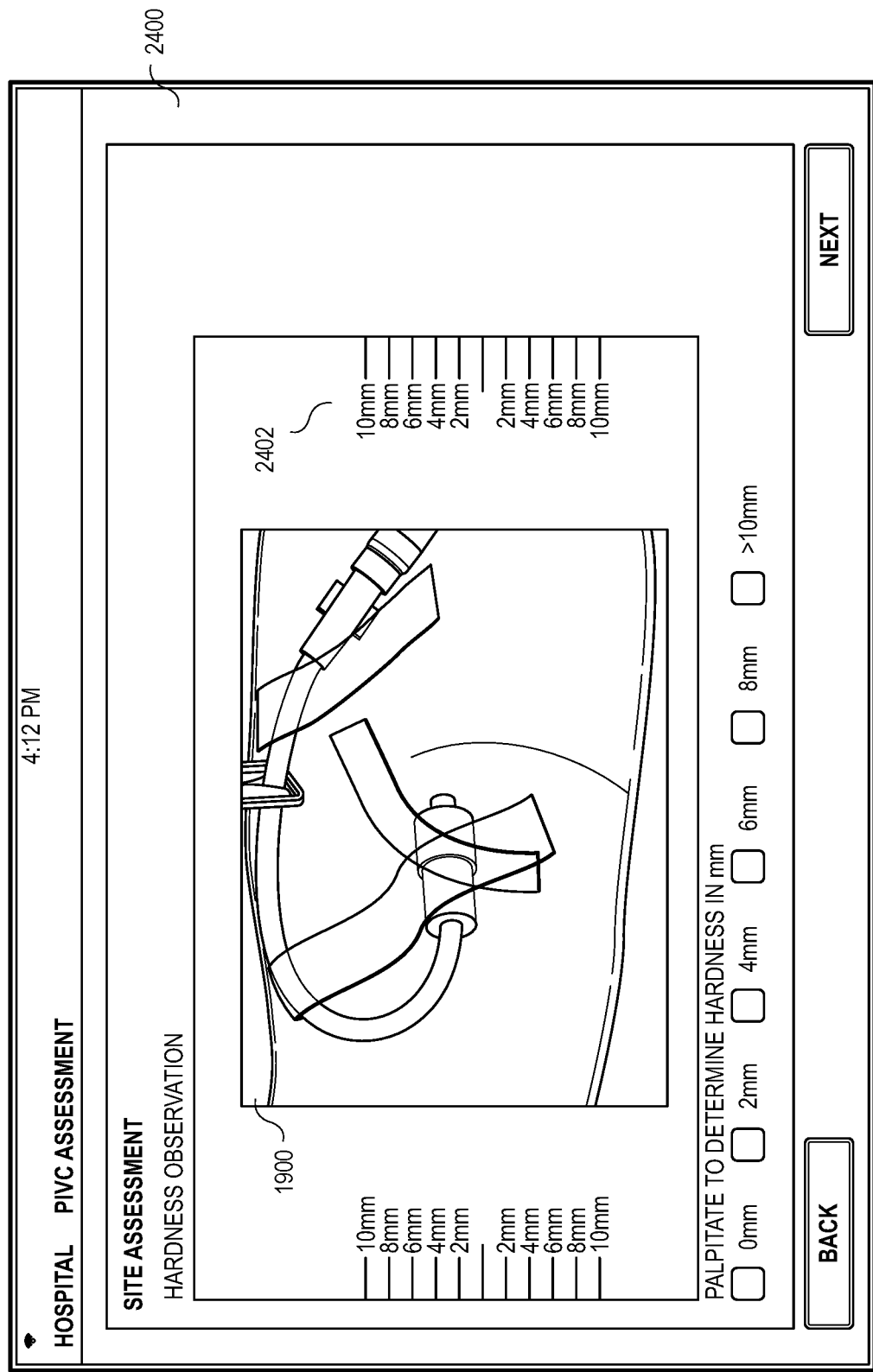
Figure 25:
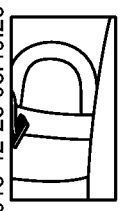
Figure 26:
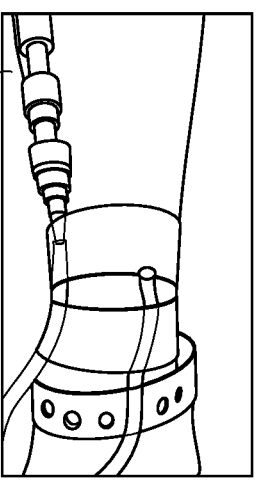
Figure 27:
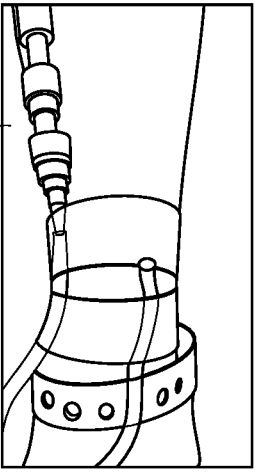
Figure 30:
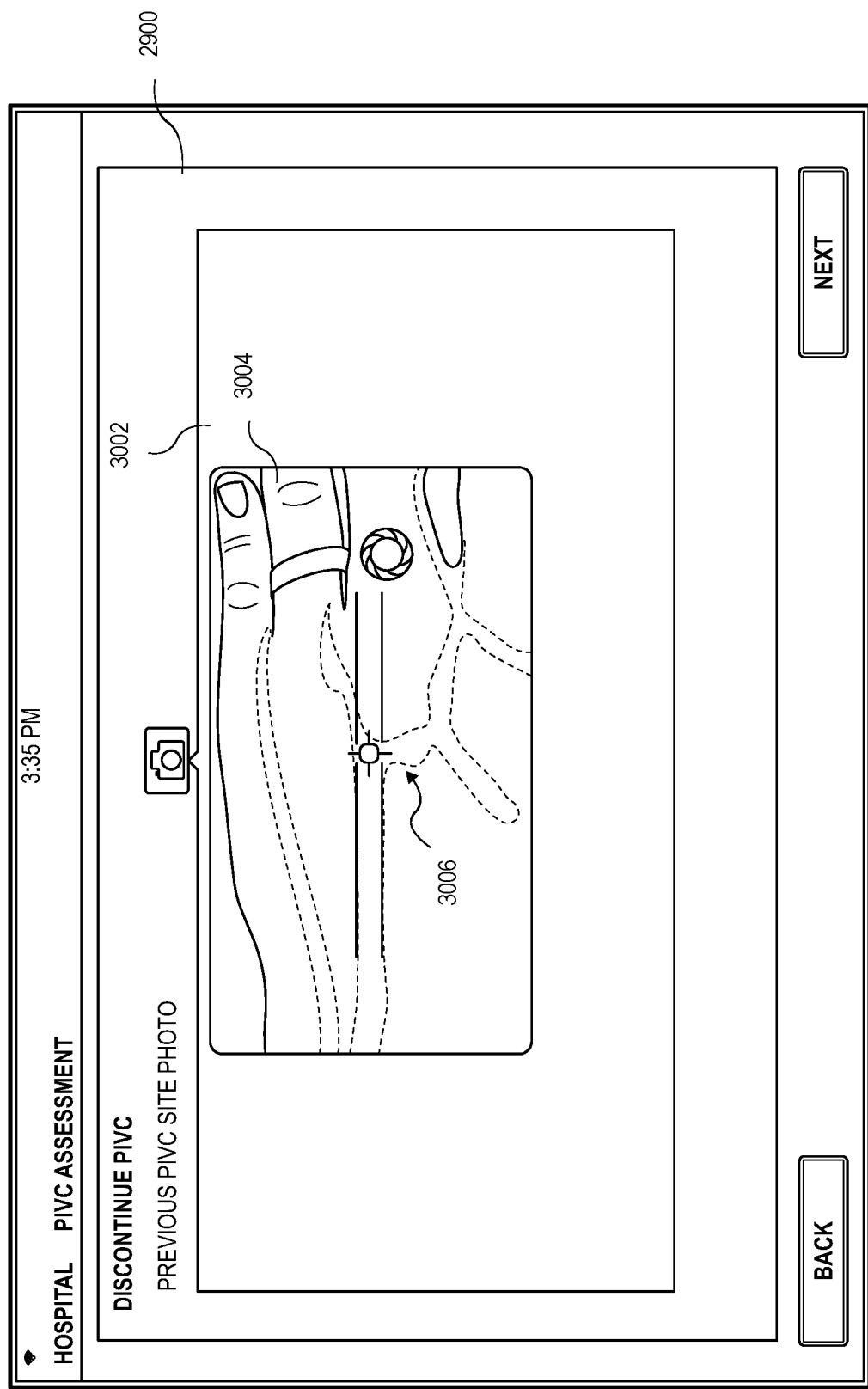
Figure 37:
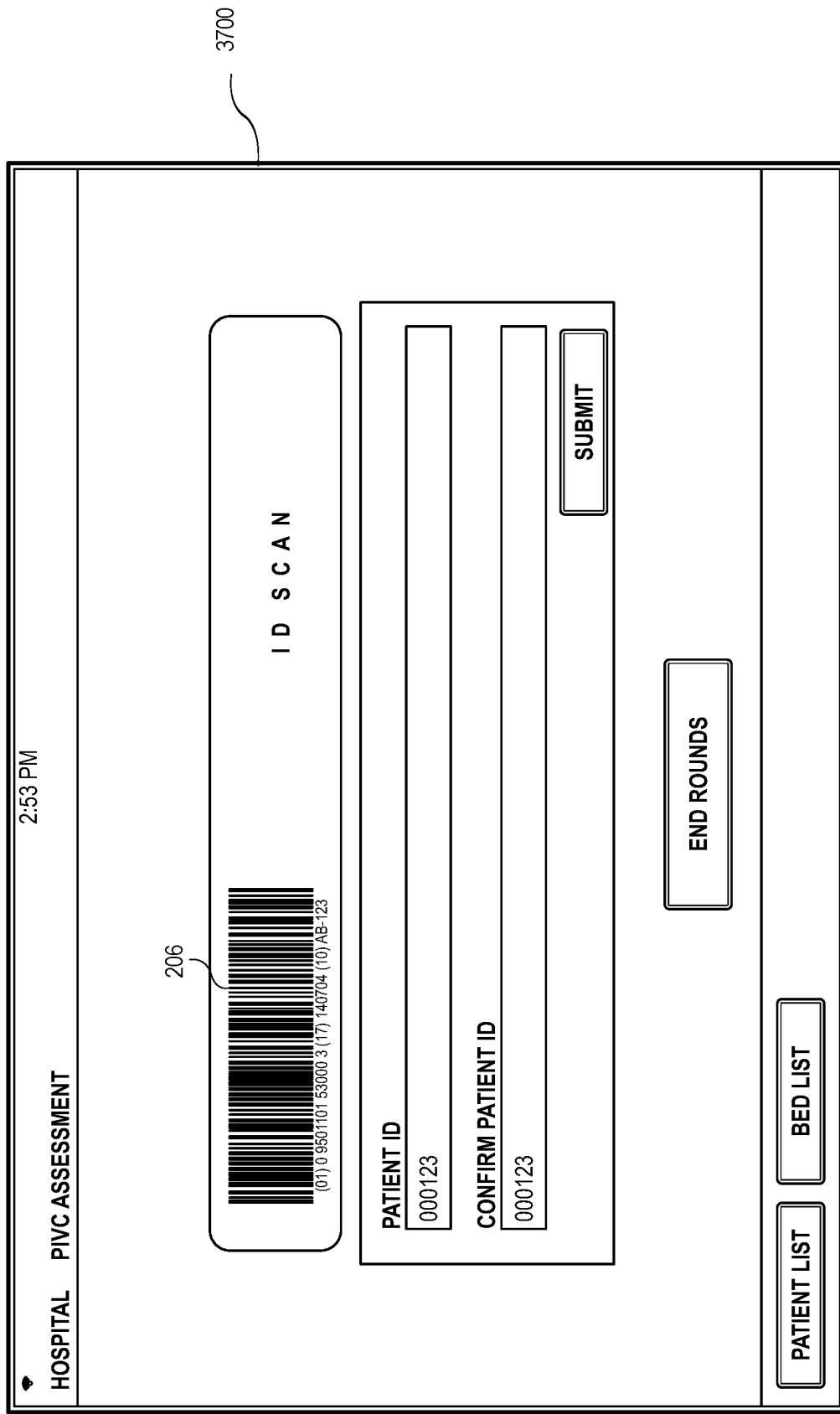
Figure 38:
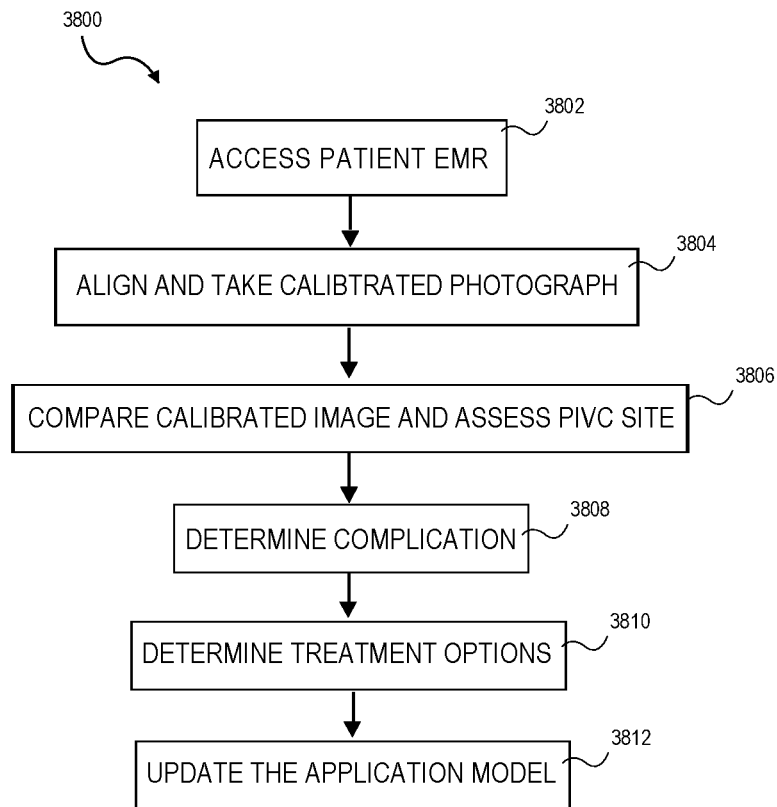
Figure 39:
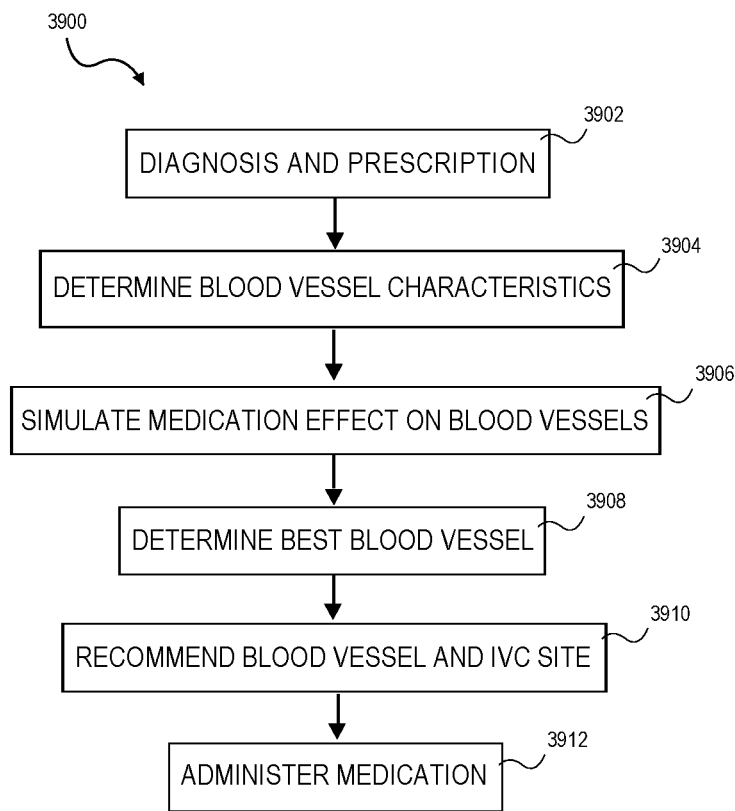

FIGS. 16A-B depicts an embodiment of the application presenting a camera image screen with a calibration zone;

FIG. 17 depicts an embodiment presenting a standard IVC;

FIGS. 18-19 depict an embodiment presenting placement of the IVC;

FIG. 20 depicts an embodiment of the application presenting a calibration image screen;

Figure 21:
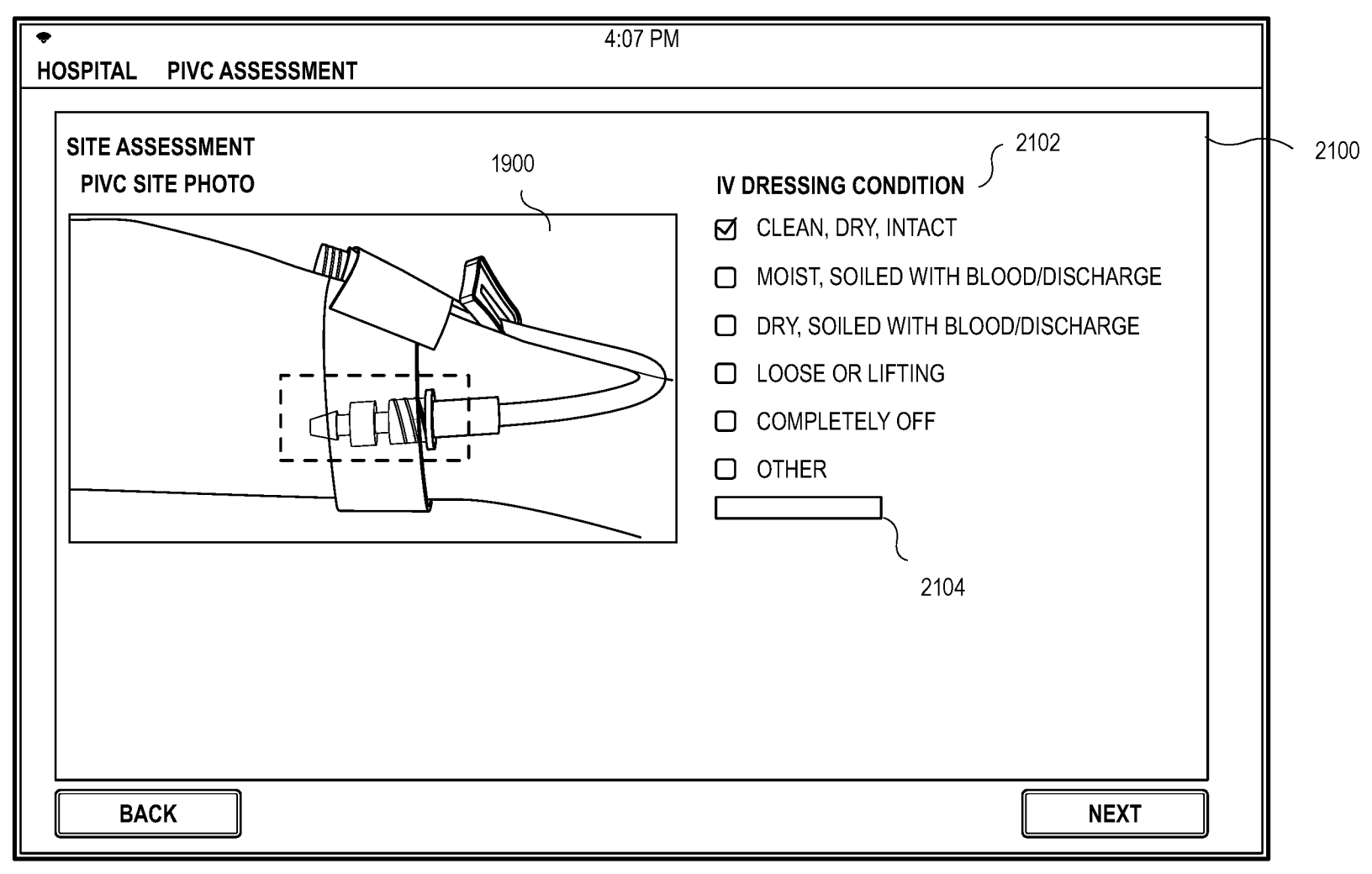

FIG. 21 depicts an embodiment of the application presenting an IVC assessment screen;

FIG. 22 depicts an embodiment of the application presenting an IVC assessment chart screen;

FIGS. 23-24 depict an embodiment of the application presenting an IVC site observation screen;

FIG. 25 depicts an embodiment of the application presenting an IVC assessment summary screen;

FIGS. 26-27 depicts an embodiment of the application presenting an IVC site complication assessment screen;

FIG. 28 depicts an embodiment of the application presenting a complications list screen;

FIGS. 29-30 depict an embodiment of the application presenting a discontinue IVC screen;

FIGS. 31-34 depicts an embodiment of the application presenting a medication administration screen;

FIG. 35 depicts an embodiment of the application presenting a questionnaire screen;

FIG. 36 depicts an embodiment of the application presenting a patient discharge screen;

FIG. 37 depicts an embodiment of the application presenting a logout screen; and FIGS. 38-39 depict flow diagrams representing methods for certain embodiments of the invention.

The drawing figures do not limit the invention to the specific embodiments disclosed and described herein. The drawings are not necessarily to scale, emphasis instead being placed upon clearly illustrating the principles of the invention.

DETAILED DESCRIPTION

The following detailed description references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the invention. The following detailed description is, therefore, not to be taken in a limiting sense. The scope of the invention is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the technology can include a variety of combinations and/or integrations of the embodiments described herein.

Figure 1:
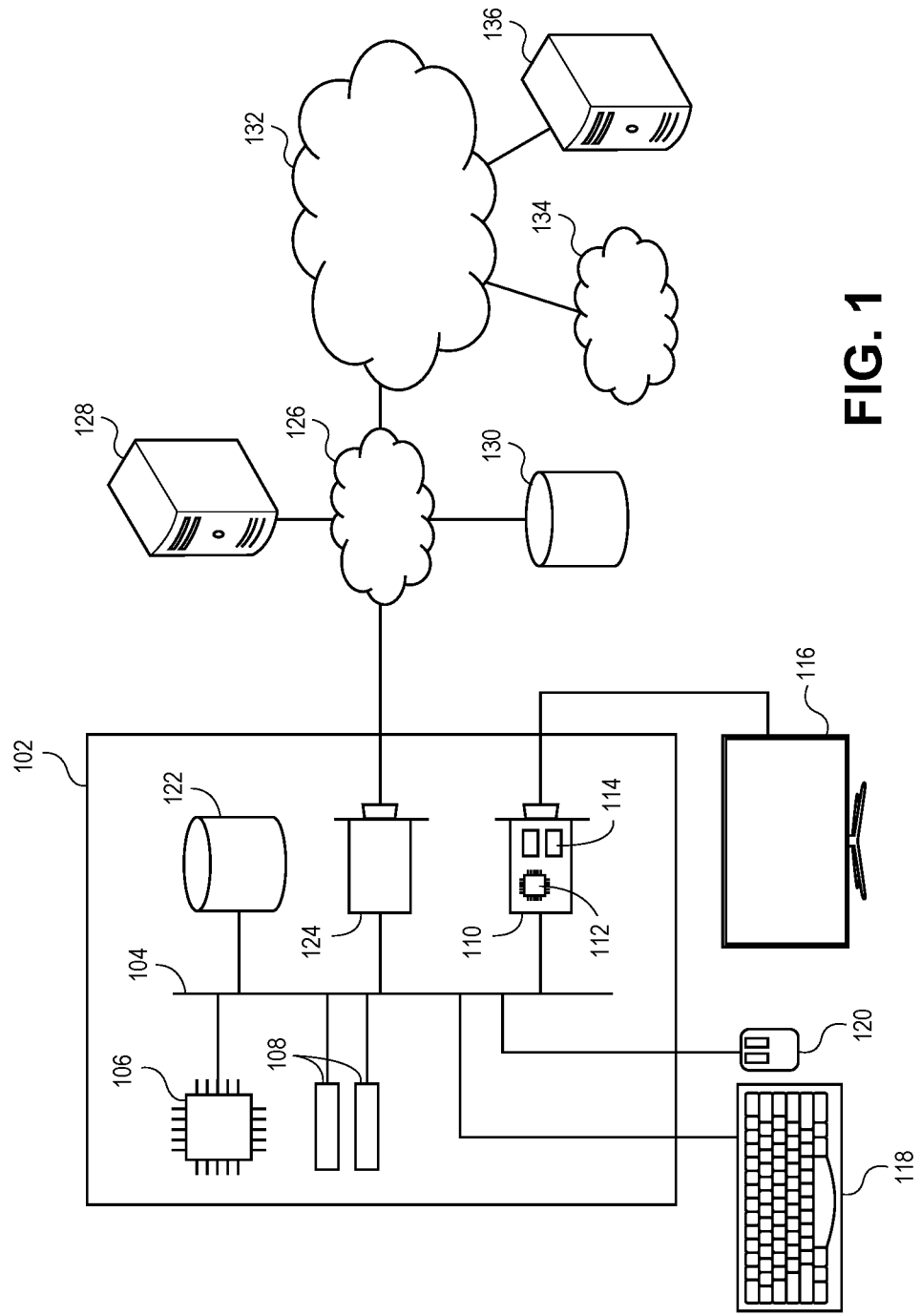
FIG. 1 depicts an embodiment of a hardware system for implementing embodiments of the invention.

Turning first to FIG. 1, an exemplary hardware platform for certain embodiments of the invention is depicted. Computer 102 can be a desktop computer, a laptop computer, a server computer, a mobile device such as a smartphone or tablet, a computer on wheels, or any other form factor of general- or special-purpose computing device. In some embodiments, the computer 102 may be an ULTRASOUND or associated with a peripheral device for performing ultrasonography. Depicted with computer 102 are several components, for illustrative purposes. In some embodiments, certain components may be arranged differently or absent. Additional components may also be present. Included in computer 102 is system bus 104, whereby other components of computer 102 can communicate with each other. In certain embodiments, there may be multiple busses or components may communicate with each other directly. Connected to system bus 104 is central processing unit (CPU) 106. Also attached to system bus 104 are one or more random-access memory (RAM) modules 108. Also attached to system bus 104 is graphics card 110. In some embodiments, graphics card 104 may not be a physically separate card, but rather may be integrated into the motherboard or the CPU 106. In some embodiments, graphics card 110 has a separate graphics-processing unit (GPU) 112, which can be used for graphics processing or for general purpose computing (GPGPU). Also on graphics card 110 is GPU memory 114. Connected (directly or indirectly) to graphics card 110 is display 116 for user interaction. In some embodiments no display is present, while in others it is integrated into computer 102 such as when computer 102 is a mobile device. Similarly, peripherals such as keyboard 118 and mouse 120 are connected to system bus 104. Like display 116, these peripherals may be integrated into computer 102 or absent. Also connected to system bus 104 is local storage 122, which may be any form of computer-readable media, and may be internally installed in computer 102 or externally and removeably attached.

Computer-readable media include both volatile and nonvolatile media, removable and nonremovable media, and contemplate media readable by a database. For example, computer-readable media include (but are not limited to) RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data temporarily or permanently. However, unless explicitly specified otherwise, the term "computer-readable media" should not be construed to include physical, but transitory, forms of signal transmission such as radio broadcasts, electrical signals through a wire, or light pulses through a fiber-optic cable. Examples of stored information include computer-usable instructions, data structures, program modules, and other data representations.

Finally, network interface card (NIC) 124 is also attached to system bus 104 and allows computer 102 to communicate over a network such as network 126 that, in some embodiments, may be a medical facility network. NIC 124 can be any form of network interface known in the art, such as Ethernet, ATM, fiber, Bluetooth, or Wi-Fi (i.e., the IEEE 802.11 family of standards). NIC 124 connects computer 102 to local network 126, which may also include one or more other computers, such as computer 128, and network storage, such as data store 130. Generally, a data store such as data store 130 may be any repository from which information can be stored and retrieved as needed. Examples of data stores include relational or object oriented databases, spreadsheets, file systems, flat files, directory services such as LDAP and Active Directory, or email storage systems. A data store may be accessible via a complex API (such as, for example, Structured Query Language), a simple API providing only read, write and seek operations, or any level of complexity in between. Some data stores may additionally provide management functions for data sets stored therein such as backup or versioning. Data stores can be local to a single computer such as computer 128, accessible on a local network such as local network 126, or remotely accessible over Internet 132. Local network 126 is in turn connected to Internet 132, which connects many networks such as local network 126, remote network 134 or directly attached computers such as computer 136. In some embodiments, computer 102 can itself be directly connected to Internet 132.

At a high level, embodiments of the invention provide a system and method for reviewing and assessing an Intravenous Catheter (IVC) insertion site. An application stored on or accessible from computer 102 which, in some embodiments, may be a mobile device such as, for example, a smartphone, tablet, computer on wheels, or any computing device, may present information associated with a patient through a patient's Electronic Medical Record (EMR). A healthcare provider may utilize a mobile device camera to take calibrated photographs and store associated calibrated images of the IVC site. The healthcare provider may compare the calibrated image with a baseline image and previously taken calibrated images to assess the IVC site. In some embodiments, the application may automatically normalize the calibrated images using light intensity and color of known objects in the images and adjust the color and lighting in the calibrated images. This may make it easier for the healthcare provider to observe differences in the IVC sites from the compared calibrated images. Further, the application may automatically analyze the images to determine any differences such as color variations, streaking, swelling, and hardness that may be indicative of complications. These differences and complications may be determined using statistical algorithms, neural networks, machine learning, or any other mathematical algorithm or artificial intelligence. The application may automatically notify the healthcare provider and emergency staff based on indications and severity of complications. The calibrated images may be stored in a database for comparison to future calibrated images. The calibrated images along with any complications, diagnosis, treatment, and results may be stored for future determination of a likelihood of complication, diagnosis, and treatment. The application may implement any statistical modeling, artificial intelligence, neural networks, and machine learning algorithms to update models for determining complications, diagnosis, and treatment suggestions.

In some embodiments, the mobile device may be computer 102 and is connected to any network as described in FIG. 1. The mobile device may be any general computing device that may be capable of connecting to the network and accessing data associated with the hospital and patients. In some embodiments, the mobile device may communicate with peripheral devices such as cameras, microphones, keyboards, GPS receivers, radio frequency identification cards (RFID), magnetic card readers, barcode scanners, or the like. The peripheral devices may also communicate with the network computer 128 presented in FIG. 1 such that the mobile device may be tracked using GPS, BLUETOOTH, and/or RFID. Device tracking and monitoring may provide a history of movements and actions and the application may use this information for scheduling and time management in embodiments of the invention discussed below.

Figure 2:
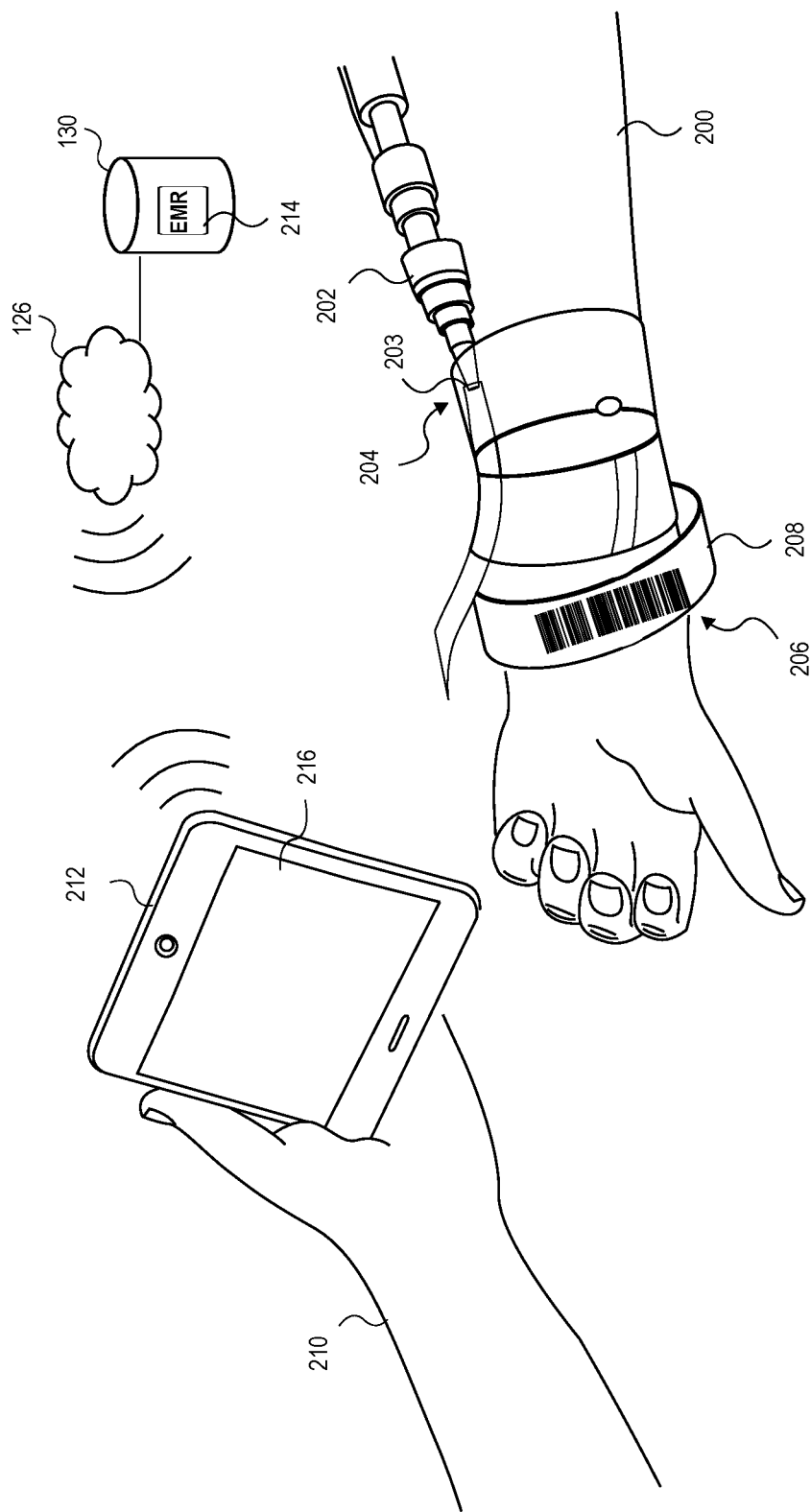
FIG. 2 depicts an embodiment of a healthcare provider interacting with a patient and utilizing a mobile device running an embodiment of an application for assessing an Intravenous Catheter (IVC) site.

FIG. 2 depicts an exemplary embodiment of a patient 200 with an IVC 202 comprising a distal hub 203 inserted into the patient 200 at an IVC site 204 and a barcode 206 attached to a wristband 208 on the patient's arm. In some embodiments the IVC 202 may be any catheter for intravenous therapy such as, for example, a peripheral catheter, a midline peripheral catheter, a peripherally inserted central catheter, and central venous catheter. A healthcare provider 210 scans the barcode 206 using the mobile device 212 comprising display 216. In some exemplary embodiments the mobile device display 216 may be display 116 presented in FIG. 1. In some embodiments, the patient's Electronic Medical Record (EMR) 214 is stored in the data store 130 of the medical facility network which, in some embodiments, is network 126 described above. The patient's EMR 214 may be accessed via a computer, the mobile device 212, or any device capable of wired or wireless connection to the medical facility network. The EMR 214 may store or be connected to or otherwise associated with a patient profile that includes patient personal information. The EMR 214 may also store the medical history of the patient 200. The healthcare provider 210 may scan the barcode 206 associated with the patients EMR 214 and the patients EMR 214 is automatically accessed via the mobile device 212. The healthcare provider 210 may enter security information such as a healthcare provider identification number to access the patient's EMR 214. Upon entry of the security information, the healthcare provider 210 may enter and edit information on the patient's EMR 214. The healthcare provider 210 may be any medical practitioner such as a physician, physician's assistant, nurse, pharmacist, or any person that provides medical care and has the necessary identification to access the healthcare facility network and the patient's EMR 214.

In some embodiments, the application may be stored on the mobile device 212 or alternatively stored in the network data store 130 and be accessible through the network 126 or accessible through network 130. In some embodiments, the application may run directly on the mobile device 212 or run through the accessible networks as a cloud based application.

Figure 3:
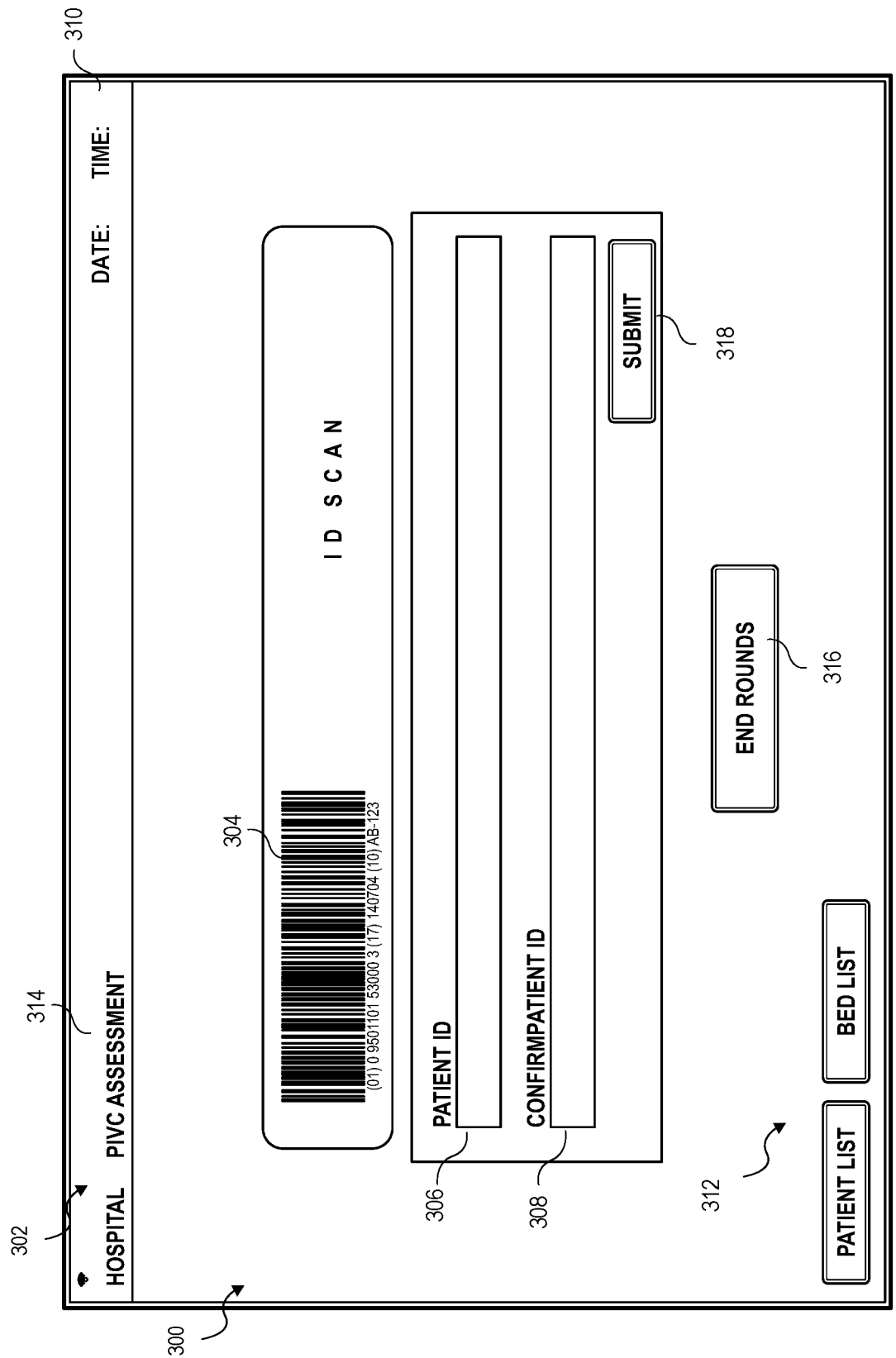
FIG. 3 depicts an embodiment of the application presenting a login screen.

Turning now to an exemplary embodiment depicted in FIG. 3 presenting a login screen 300 displayed on the mobile device 212 and generated by the application. The page descriptor 302 may present a digital barcode 304 associated with a patient identification number 306 and a confirmation field 308 for verification of the patient identification number 306 by the healthcare provider 210. The patient login screen 302 may present a location identifier, a date and time field 310, and links 312 to other pages of the application. The application may also present a task 314 being performed. For example, the task 314 may be rounds, or a periodic check on patients or administration of a treatment such as bandage replacement, medicine administration, or an IVC assessment as indicated on the login screen 300. In some embodiments, the healthcare provider 210 directly enters the patient identification number 306. In other embodiments, the barcode 204 associated with the patient 200 is scanned and the application accesses the patient's EMR 214 from the stored database. The healthcare provider 210 may exit the login screen by selecting an exit button 316, for example the end rounds button presented in FIG. 3.

In some embodiments, the physical barcode 204 is scanned and the application may automatically connect to the patient's EMR 214 or, for security purposes, the system may prompt the healthcare provider 210 to input information to access the patient's EMR 214. Once the healthcare provider 210 has entered the necessary security information, the healthcare provider 210 may verify the patient ID number 306 and personal information. In some embodiments, the healthcare provider 210 may verify the patient's identity by asking the patient 200 personal information such as birthday, social security number, any identification number, and any information related to any physical feature. The questions may be displayed by the application and the healthcare provider 210 may ask the patient 200 and enter the information manually. A warning may be issued via the mobile device 212 if there is a discrepancy between the information supplied by the healthcare provider 210 and the stored personal information associated with the patient 200. Upon confirmation of the patent information the healthcare provider 210 may select several options including; end rounds, submit information, patient list, or bed list, which may be linked to other screens provided by the application and associated with the selected option. In some embodiments, the login screen 300 may present many more options such as back, next, home, or a navigation, or link, to any page or screen presented by the application. The options may be presented in a scroll-down or a dropdown menu or accessible by any button or icon presented on any displayed screen.

Figure 4:
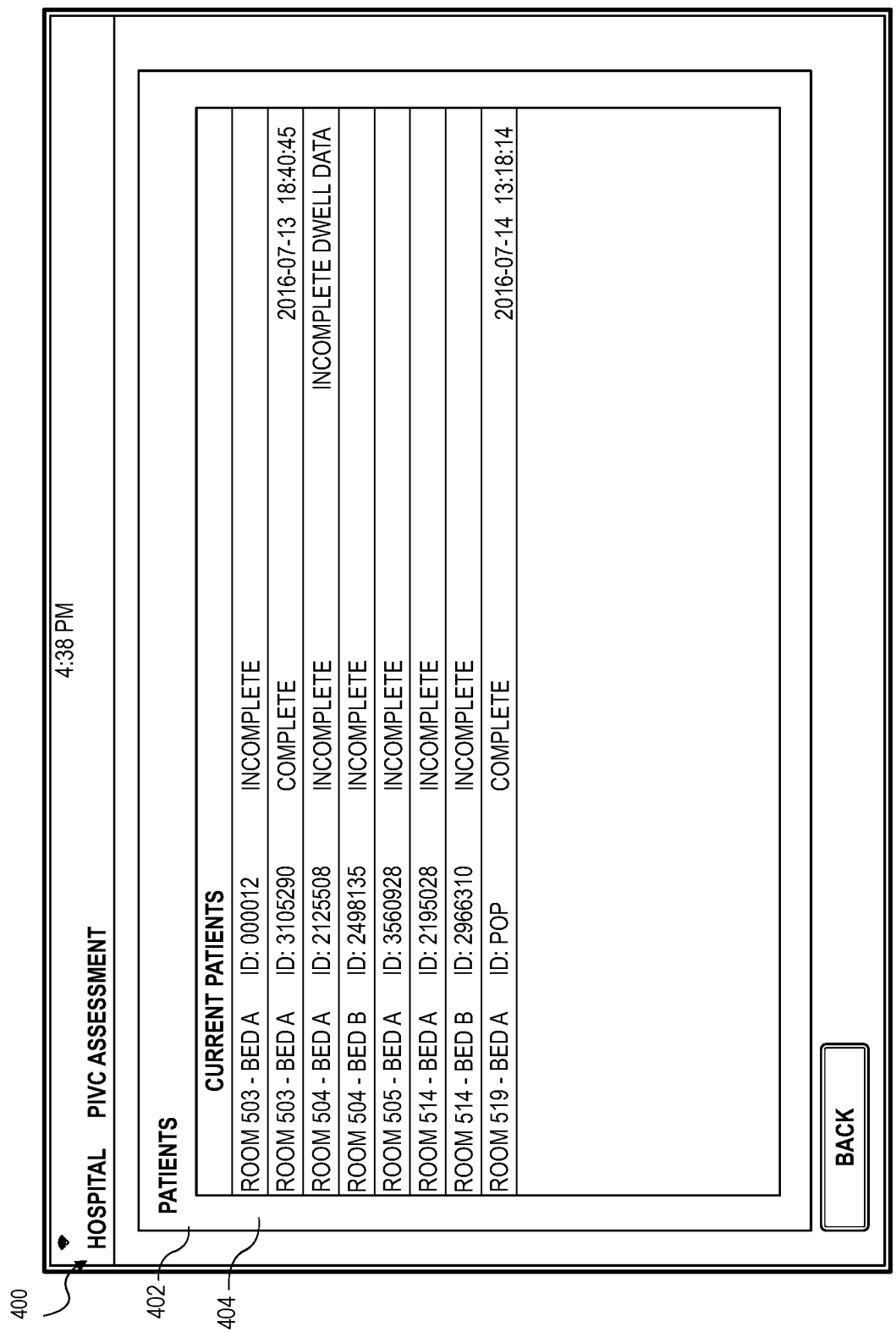
FIG. 4 depicts an embodiment of the application presenting a patient list screen.

Turning now to FIG. 4 depicting a patient list screen 400 in which information associated with a plurality of patients 402 is displayed via the display 216 on the mobile device 212. The patient list screen 400 may present a patient list 402 including patient information 404 and associated information such as a patient room, bed indication, patient identification number, progress and discharge information. Any other information associated with the patient 200 may be presented such that the status of the patient 200 may be displayed or otherwise accessible to the healthcare provider 210 through the patient list screen 400. The healthcare provider 210 may select any displayed button or item displayed on the patient list screen 400 to advance the application to a screen providing more in-depth information related to the selected item. For example, if the patient 200, with associated ID: 3105290, is changing rooms, the healthcare provider 210 may select the room number or the patient ID number on the patient list 402 and either edit the information directly via the displayed screen or be directed to a different page presenting editable information associated with the selected patient.

Figure 5:
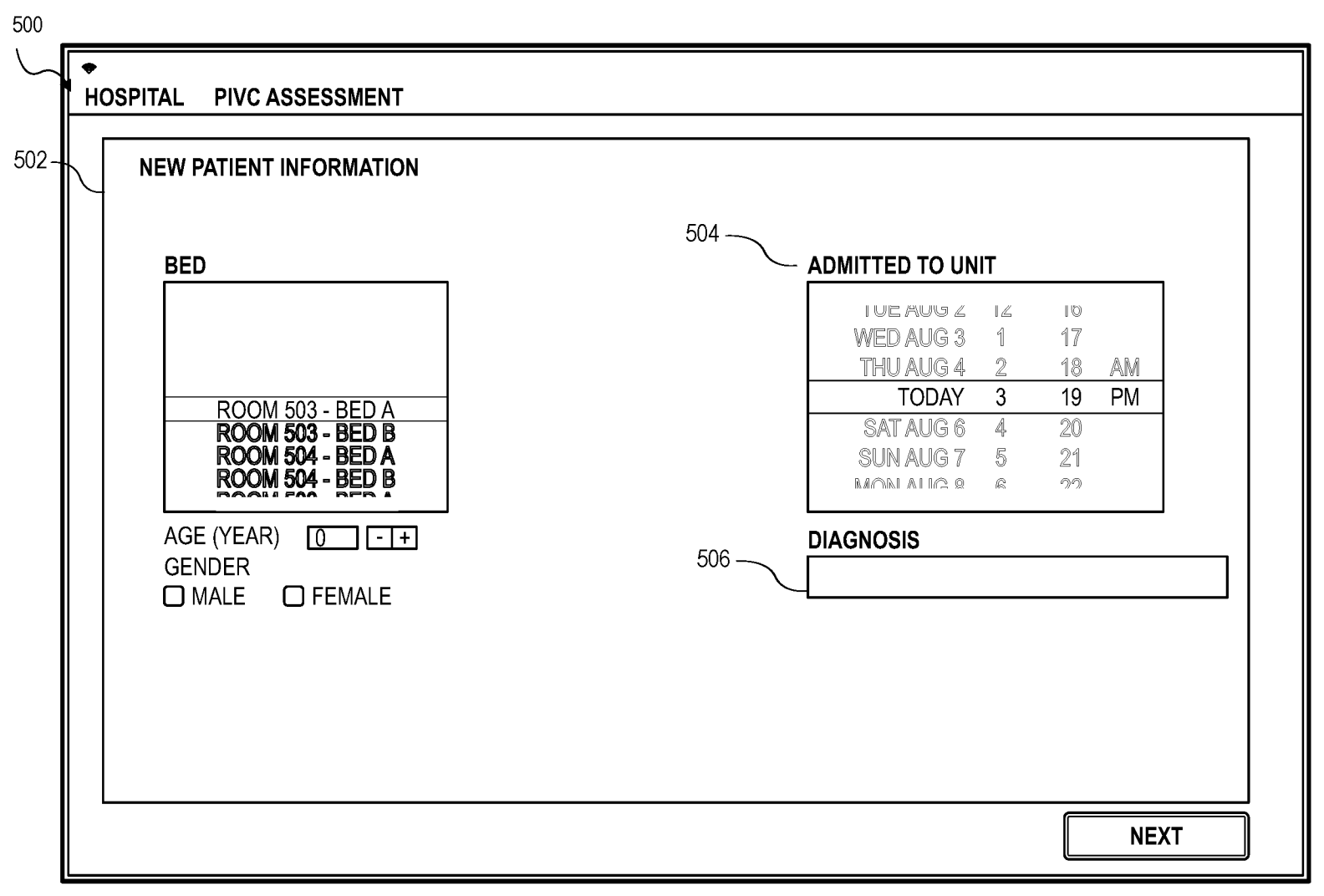

Turning to FIG. 5 depicting a new patient information screen 500 in which the patient 200 may be admitted to the system and receive the IVC 202. The patient information may be added manually or the application may connect to the patient's EMR 214. The patient location information 502 and the time and date 504, unit, and any additional information associated with the patient 200 may be added or edited on the new patient information screen 500. Further, any symptoms, diagnosis, or causes may be added or edited and any notes may be provided in the diagnosis field 506.

Figure 6:
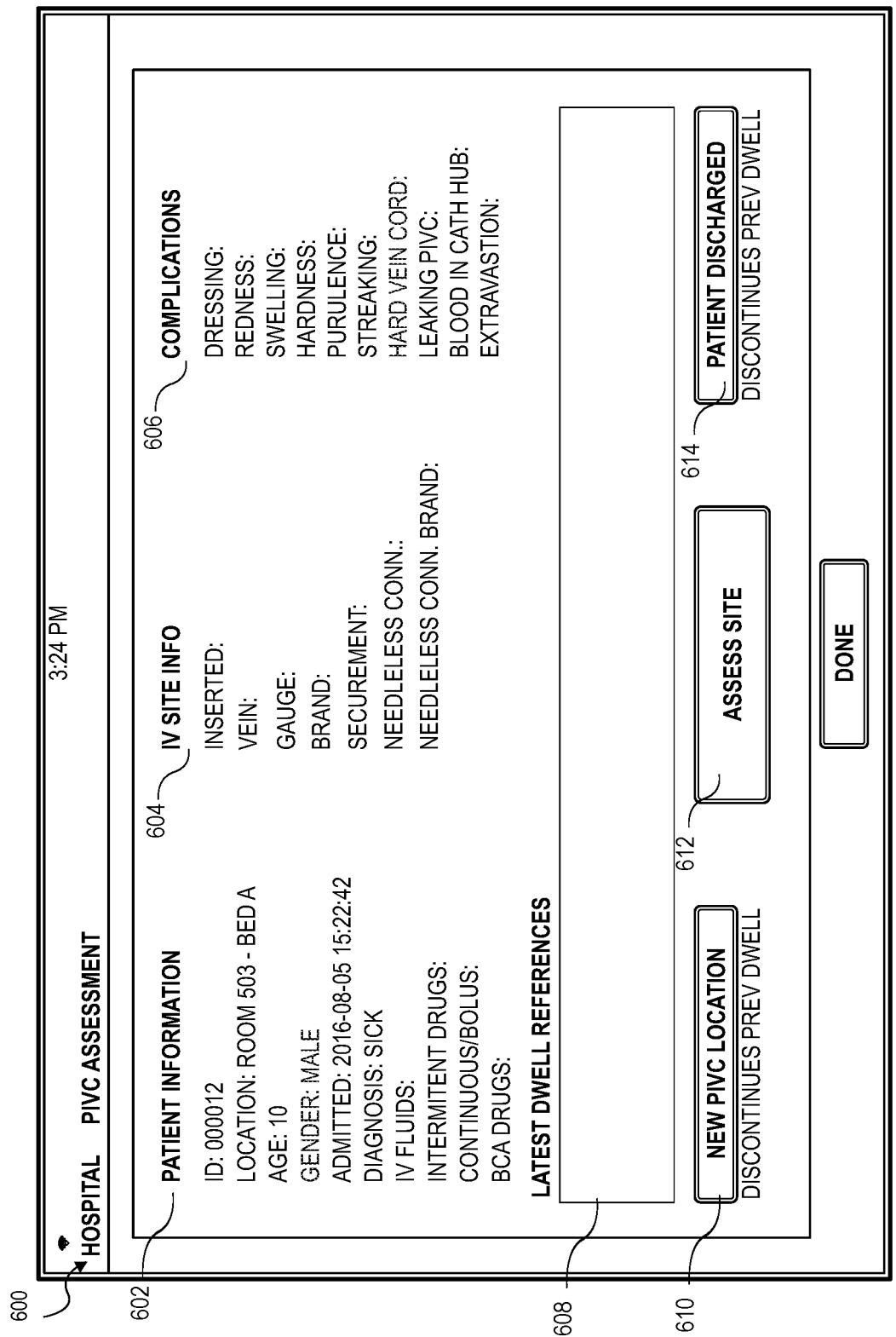
FIG. 6 depicts an embodiment of the application presenting a patient information summary screen.

Turning to FIG. 6 depicting a patient information summary screen 600, the application displays patient information 602, IVC site information 604, and complications information 606. The patient information summary screen 600 may also display an IV dwell time and any information associated with the dwell time in a dwell references editable field 608. The patient information summary screen 600 may also provide buttons for adding a new IVC, assessing a current IVC site, and discharging the patient 200. In some embodiments, the buttons may provide a link to a page that presents information indicative of the selected button. For example, the healthcare provider 210 may select New IVC Location button 610, an assess site button 612, or a patient discharge button 614, and the application may present a screen associated with the selected button for presenting and receiving information related to the selected topic.

Figure 7:
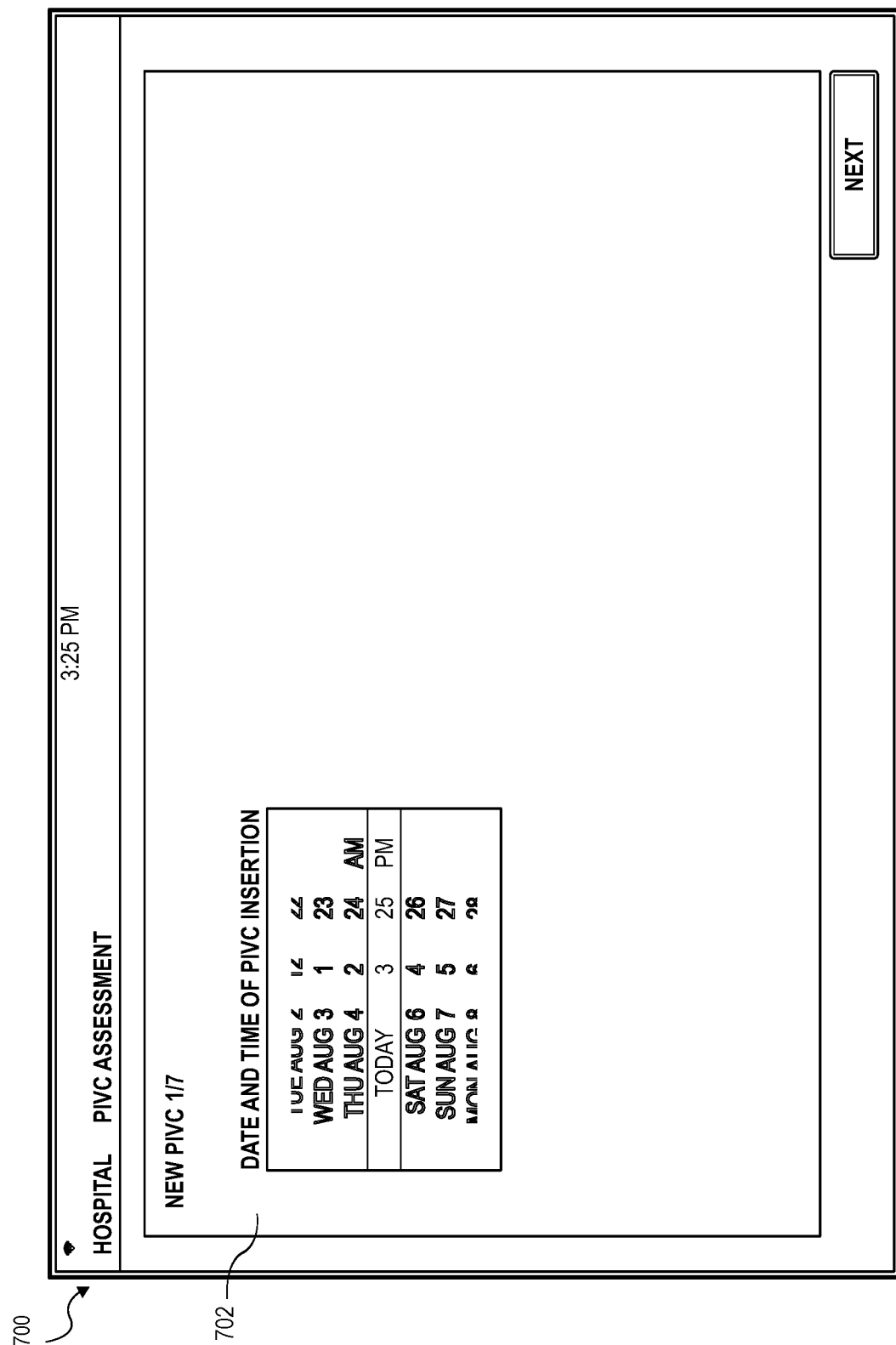
FIG. 7 depicts an embodiment of the application presenting an IVC selection screen.

FIG. 7 depicts a new IVC selection screen 700 presenting a time and date selection 702 for a new IVC insertion. The new IVC selection screen 700 may be accessed when the patient 200 is receiving the first IVC 202 of the patient's stay at the medical facility or when a previously administer IVC is discontinued.

FIG. 8 depicts an embodiment of a new IVC placement screen 800 for adding information related to the IVC 202 insertion. The new IVC placement screen 800 may provide clinician fields 802 for presenting known healthcare providers and/or receiving the healthcare provider 210 name, title, or identification number. A unit field 804 allowing input of a location and associated information may be input. A comments field 806 may be provided for receiving any information such as comments, new catheter information, redress, or any reason why the redress was necessary. The healthcare provider 210 may also save the record 808, or all information input thus far, and perform the task at a later time. An alert may be issued through the application to remind the healthcare provider 210 that the task 314 needs completed.

In some embodiments, the new IVC placement screen 800 may also provide an ultrasonography field 810 for the healthcare provider to input if ultrasonography was used in deciding the placement of the IVC 202. In some embodiments, ultrasonography may be used to determine the flow of blood through vessels. Blood flow characteristics may provide information related to the vessel's ability to receive an IVC 202 or particular medications that may be provided through the IVC 202. The application may be connected to a device for performing ultrasonography and receive information for determining a best vessel to insert the IVC 202 or the healthcare provider 210 may input the information received from ultrasonography. The blood vessel and blood flow characteristics may be used to create a Computational Fluid Dynamics (CFD) model of the vessel. Different blood vessels may be modeled using blood vessel characteristics and characteristics of an intended intravenous fluid or prescribed medication and determine an optimal rate at which the intravenous fluid is to be introduced into the blood vessel. The application may then combine all information to determine the best blood vessel to be used for the patient 200 based on the information gathered via the ultrasonography and the CFD model and analysis.

Figure 9:
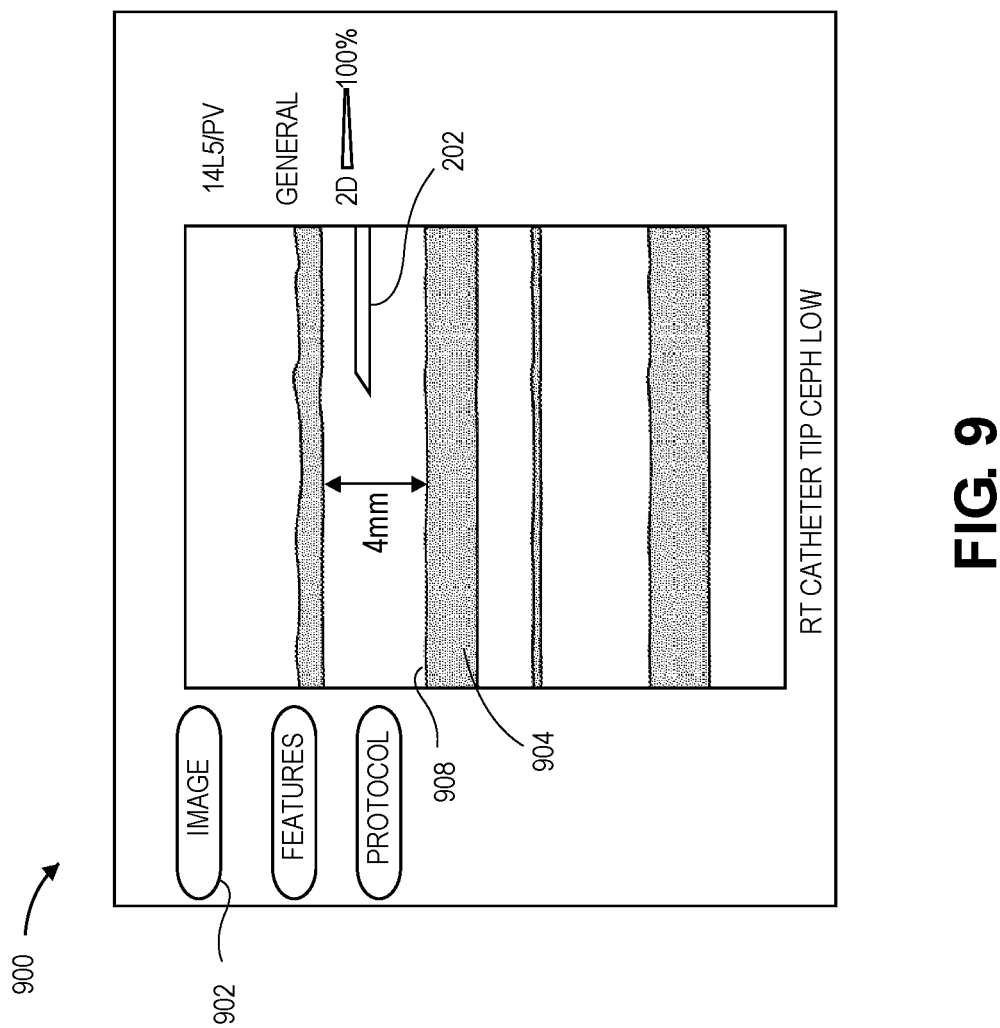
FIG. 9 depicts an embodiment of a blood vessel and IVC image from ultrasonography.

FIG. 9 depicts an exemplary ultrasonography screen 900 presenting a digital image 902 of a blood vessel 904 and IVC 202 from ultrasonography. The digital image 902 is an exemplary image obtained from ultrasonography for capturing blood vessel characteristics for the CFD model described above. In some embodiments, experimental data is collected by measuring the medication injected/infused into the blood vessel 206 and the resulting medication effect indicative of pH and osmolality of the combination of the blood and medication in the blood vessel. In some embodiments, the medication effect also comprises an effect on the interior wall 908 of the blood vessel such as, for example, deterioration. In some embodiments, the data is collected experimentally over time, for example, over the course of a patient's stay at a medical facility while receiving treatment. This data may be collected over a plurality of studies and patients and statistical analysis performed to determine the blood vessels, medications, medication injection rates, blood pH, and osmolality that were closest to optimal. In some embodiments, the data is obtained through simulations of the blood vessel with injected medication. In some embodiments, optimal may be a result in which osmolality and pH are balanced in the blood with the least amount of deterioration to the blood vessel. In some embodiments, optimal may be closest to the preferred infusion rate of medication while minimizing the medication effect on the blood vessel. Simulations comprising CFD models utilizing blood vessel characteristics, blood flow characteristics, and medication infusion may be to determine an effect of the medication on the blood flow and the interior wall of the blood vessel.

In some embodiments, a hemodilution ratio/factor is used to determine the rate of dilution of the medication in the blood. A high concentration of a low pH medication may be caustic to the blood vessel 904 as discussed above. To lower the risk of deterioration of the blood vessel 904, the caustic medication may be diluted by the blood as quickly as possible. Local and immediate dilution of the medication in the blood may lessen the risk to the blood vessel 904. As the medication is introduced into the blood vessel 904 the rate of dilution describes the rate of pH stabilization and osmolality of the blood. In some embodiments, the hemodilution ratio, or hemodilution factor, may be described by the blood flow proportional to the infusion solution (medication) flow. The hemodilution ratio provides a quantifiable relationship between the blood vessel characteristics, the blood flow, and the medication. An optimal hemodilution ratio may be determined using the blood vessel characteristics measured by ultrasonography and the medication introduction into the blood vessel. The optimal hemodilution ratio may, in some embodiments, minimize the effect of the medication on the blood vessel by determining an optimal infusion rate of the medication based at least in part on a change in the pH and a change in the osmolality of the blood and blood flow combined with the medication.

A variety of hemodilution ratios may be simulated to determine the best range of infusion rates and the best blood vessel and location for injection of the medication. Some factors in the system are variable such as, for example, the diameter of the blood vessel 904 and the blood flow. These factors may change at different blood pressures, temperatures, velocities, and blood flow rates and medication flow rates. The difficulty in modeling such variances may result in a range of possible "best" solutions for the hemodilution ratio. Different hemodilution ratios based on medication infusion rates and blood flow may be tested in the CFD simulations. Based on the medication effects from the simulation results a range of hemodilution ratios, and resulting medication infusion rates, may be determined and recommended by the application.

The recommendation for medication infusion rates may be based on treatment. For example, a dilution ratio, or hemodilution ratio, comprising blood flow in mL/min and infusion solution flow in (mL/min) may be used to determine the blood to solution or hemodilution ratio. A range of hemodilution ratios may be simulated to determine a range of medication effects based on the blood flow and the medication infusion rate. Thresholds may be determined and labeled for recommendation. For example, where no irritation to the blood vessel is expected the hemodilution ratio, and medication infusion rate, may be labeled gentile. A more aggressive medication infusion rate, or more caustic medication, may result in a hemodilution ratio labeled borderline. This borderline infusion rate may be avoided if possible. An even more aggressive medication infusion rate, or more caustic medication, may result in an aggressive label, meaning that this infusion rate should be avoided.

In some embodiments, the medication effect, for example, the osmolality, or quantity of dissolved particles such as, for example, salt, and the pH of the blood may be simulated using mathematical relationships as well as experimental data as described above. An optimal balance of osmolality and pH may be compared to the results of the simulation to determine a blood vessel that provides the closest to optimal results. The blood vessel and injection location that provides results closest to optimal based on the medication, medication rate, and blood vessel characteristics simulated in the CFD model may be recommended for the IVC site 204. The medication effects such as a rate of dilution, medication dispersion, which effects the osmolality and the pH of the blood and the caustic effects on the blood vessel 904 may be determined from the blood vessel characteristics and the blood flow characteristics as well as medication flow in the CFD simulation. Optimal medication concentrations and input rates may be determined based on the medication effect on the blood vessel and blood in the simulation such as the osmolality and the pH of the blood and the medication injection/infusion rate as determined by the hemodilution ratio as described above. The best blood vessel and the location for the IVC may be determined from the simulations based on the medication effect such as, for example, a change in the combined blood flow and medication flow, osmolality, and pH of the blood and medication combination in the blood vessel 904.

In an exemplary scenario, a doctor may evaluate the patient 200 and prescribe medication based on a diagnosis. The prescribed medication may be, for example, vancomycin. The prescribed vancomycin has a pH of between 2.5 and 4.5. The acidity of the vancomycin may be caustic to the vein, therefore increasing the importance of the vein selection.

Typically, healthcare providers administer drugs at an easily accessible vein starting at the wrists and, when complications occur, moving up the arm accessing different veins. This is a technique that may result in several IVCs and patient sticks before the medication is fully administered. This results in high costs and low patient satisfaction and is avoidable utilizing the techniques and vein analysis described in embodiments herein.

Once the doctor has prescribed the medication, the pharmacist may fill the medication and send the medication along with procedural instructions for administration of the medication to the healthcare provider 210.

Through the use of ultrasonography, Doppler radar images or ultrasonographic images (e.g. the digital image 902) and video may be utilized to determine the blood vessel characteristics such as, for example, the size of the blood vessel 904. Blood flow characteristics, such as, velocity, viscosity, turbulence, and flow rate may be necessary in determining how the medication will interact with the blood and the blood vessel. In some embodiments, blood vessel characteristics and blood flow characteristics essential to CFD modeling may comprise vein size and blood velocity. In some embodiments, the blood vessel characteristics may comprise blood vessel diameter, elasticity, and any other blood vessel characteristic that may be useful in determining a best blood vessel and location to receive the medication. In some embodiments, the blood vessel characteristics may also comprise blood flow characteristics. The blood flow characteristics may be blood velocity, blood flow rate, viscosity, blood pressure, blood temperature, turbulence, and any other blood flow characteristics that may be useful in determining the best blood vessel and IVC location. In some embodiments, any blood flow characteristics may be estimated as described above and the blood flow characteristics may be simulated in the CFD model.

The ultrasonography may be administered by the healthcare provider 210 before or after the prescription and/or the pharmacist fills the medication. The ultrasonography device may be portable and provided with a mobile device such as, for example, a tablet, smartphone, laptop, and a computer on wheels. The application performing the CFD analysis may be stored on and run by the mobile device or may be run as a cloud-based application. The application may store the results in a database associated with the application and separate from the patient's EMR 214. In some embodiments, the results of the ultrasonography may be stored in a database associated with the application or stored in the patient's EMR 214 for future use. Further, the ultrasonography results may be downloaded from the patient's EMR 214, the application database, or any online database for use in the CFD simulation as described below.

The results of the ultrasonography may be automatically loaded or manually input into CFD models and the patient's EMR 214 to simulate the medication in the blood vessel 904 and determine how the prescribed medication interacts with the blood and the blood vessel 904. For example, the blood vessel 904 may be modeled using the blood vessel information and/or characteristics collected during the ultrasonography and the medication modelled in the simulation. In the simulation, the medication may be added to the blood vessel 904 at various rates, concentrations, and locations.

In some embodiments, a plurality of blood vessels may be simulated and the blood vessel that receives the highest, or otherwise doctor prescribed, concentration of medication while showing the least negative medication effects may be rated as the most desirable blood vessel for intravenous treatment of the medication. A list of best performing blood vessels, based on the analysis and simulation, may be created to provide the healthcare provider 210 with a plurality of options and a range of hemodilution factors and medication infusion rates for administering the medication.

In some embodiments, the best blood vessel and location along the blood vessel for insertion of the IVC as well as the medication infusion rate may be included in the procedural instructions provided to the healthcare provider 210. In some embodiments, a list of a plurality of blood vessels with rankings from most desirable to acceptable as well as medication infusion rates and medication concentrations from aggressive to gentle may be provided and recommended by the application.

In some embodiments, FIG. 9 depicts an exemplary chart and image depicting blood vessel 904 such as, for example, veins or arteries to administer a particular prescribed medication via the IVC. The best blood vessel may be determined through the CFD analysis of the blood vessels of the patient 200 as described above.

Figure 10:
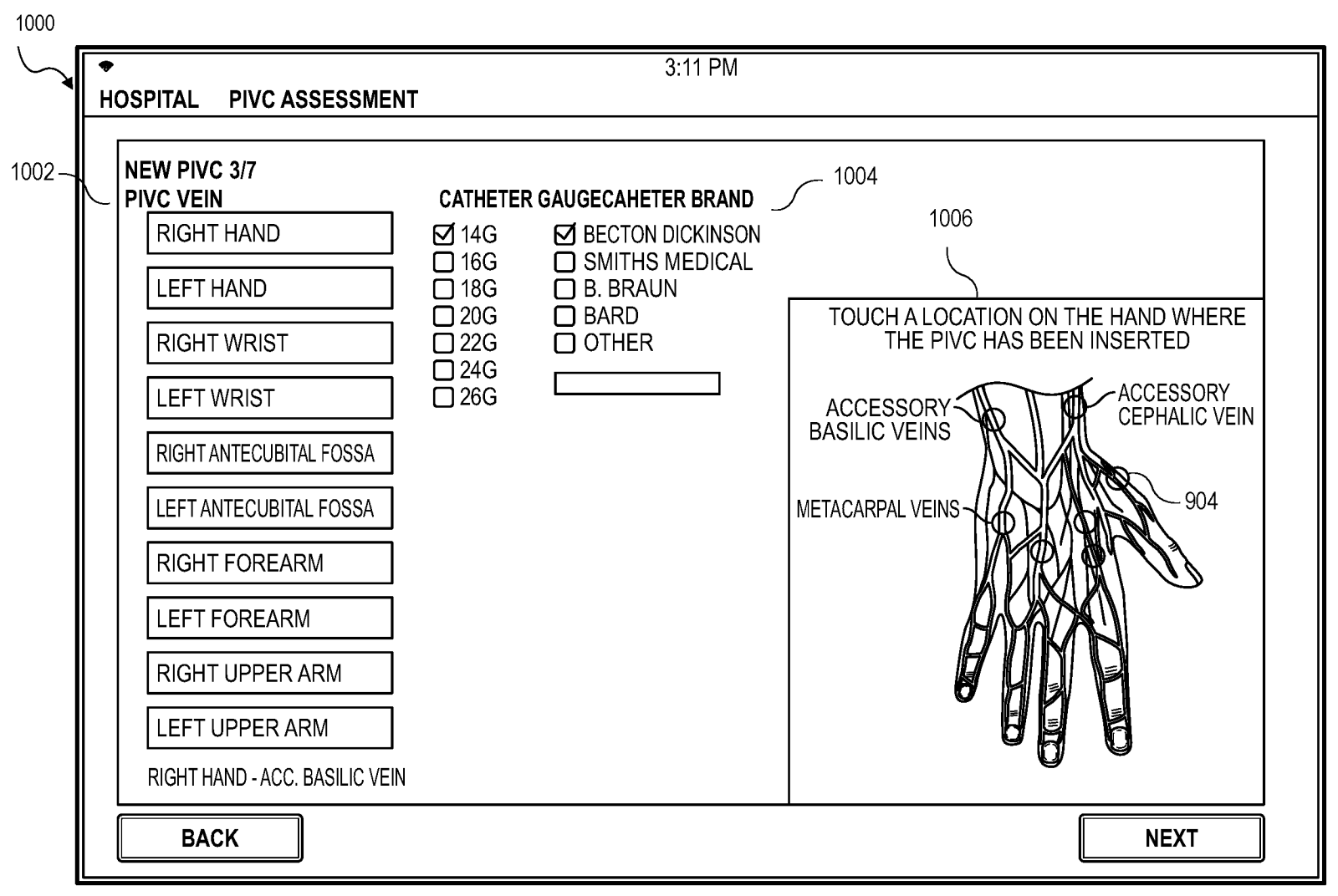

Continuing with FIG. 10 presenting an exemplary embodiment of a new IVC vein location screen 1000 for receiving information related to the new IVC and IVC insertion location. In some embodiments, the application presents a location field 1002 for the location of the vessel and a catheter field 1004 for receiving the gauge of the catheter and the brand of the catheter. In some embodiments, the information provided on the new vein screen 1000 may be determined by the application from the CFD analysis described above and presented to the healthcare provider 210 for verification. The application may also present a graphic 1006 of a hand with the veins visible and the healthcare provider 210 may select the vein to be used by touching the graphic 1006. In some embodiments, the hand depicted in the graphic 1006 is an image of the patient's hand the healthcare provider 210 may indicate an area for insertion of the IVC 202 by touching the screen.

Any information provided and received via the IVC vein location screen 1000 may be used in calibrating a photograph of the IVC site 204. For example, information such as an image of the gage and brand of the IVC 202 may be stored in the data store and accessible by the application. When the gage and brand of the IVC 202 is selected from the catheter field 1004, the application may automatically select and store information related to the catheter for future use. This may provide quick access to information for targeting the size and shape of the IVC 202 for calibrating a photograph to be taken of the location of the IVC 202 insertion.

In some embodiments, the graphic 1006 may present the blood vessel 904 along with a measurement of the blood vessel 904 such as, for example, a measured diameter of the blood vessel 904. The diameter of the blood vessel 904 may be measured using the calibrated image and a digital measurement chart as described in detail in reference FIG. 21 below. Once the diameter of the blood vessel 904 is determined the CFD model may be utilized to determine if the blood vessel 904 is the best blood vessel 904 for the prescribed medication as described in embodiments above.

FIG. 11 depicts a page for presenting and receiving information related to the new IVC 202 insertion. The skin preparation screen 1100 may receive information related to preparation prior to insertion of the IVC 202. Any skin preparation and any IV kit used may be entered in the skin preparation field 1002 and the IV field 1104 as well as any comments by the healthcare provider 210 may be provided in the comments field 1106.

FIG. 12 provides an IVC site dressing screen 1200 displaying a dressing type field 1202 for receiving input related to the dressing type. Further dressing information is provided via the IVC site dressing and securement screen depicted in FIG. 12. The IVC site dressing and securement screen 1300 may receive input related to the securement via a securement field 1302, connector via a connector field 1304, and brand via a brand field 1306, or a barcode associated with the connector may be scanned and the application may be automatically updated with the information. The IVC site dressing and securement screen 1300 may also receive any comments or suggestions for future reference and to store the comments and any input in the patient's EMR 214. Further, the healthcare provider 210 may be automatically prompted to verify the connector or input the connector and securement information.

FIG. 14 depicts a disinfection screen 1400. The disinfectant screen 1400 is configured to receive, from the healthcare provider 210, information related to the disinfection of the hub/port of the catheter and connector via the disinfection field 1402. The disinfectant procedure is necessary to lessen the risk of a blood infection when the IVC 202 is inserted into the patient's vein. Providing the information on this page verifies that the proper steps have been taken and stores the information related to disinfection for analysis upon removal of the IVC 202 or when a complication is detected.

FIG. 15 provides a complete patient summary screen 1500 as described in relation to the incomplete patient summary screen provided in FIG. 6 above. Similarly, the application displays patient information 1502, IVC site information 1504, and complications information 1506. The healthcare provider 210 may review the summary screen 1500 to verify that all information has been entered and is correct. The healthcare provider 210 may edit any information and supply any comments and notes on the summary screen 1500. Alternatively, the healthcare provider 210 may select any item on the summary screen 1500 and automatically be linked to a more descriptive page related to the selected item. In some embodiments, the healthcare provider 210 may edit fields from the linked page. For example, the healthcare provider 210 may notice that the IV brand 1508 is listed as Nexus TKO-6P. The healthcare provider 210 may select IV Brand 1508 by either touching the screen at the location of the label, select using an icon, or select by scrolling through the labels. Once selected, the application may automatically open the securement and connector screen 1200 presented in FIG. 12. At this point the healthcare provider 210 may edit the IV brand in the brand field 1206 which automatically updates the application and the patient's EMR 214. The healthcare provider 210 may then return to the patient summary screen 1500 to verify that the edit is stored.

FIG. 16A depicts a camera image 1600 provided by the camera of the mobile device 212 on the mobile device display 216 including a calibration zone 1602. The image 1604 shows the patient's hand with the calibration zone 1602 superimposed on the image 1604. The calibration zone 1602 may be used to visually match to an object with a known dimension in the image 1604. As the healthcare provider 210 moves the mobile device 212 the image 1604 shows the information in the camera frame. The calibration zone 1602 may be static on the display 216 such that the mobile device 212 may be moved to match a dimension in the image 1604 with the calibration zone 1602. The calibration zone 1602 is discussed in detail below.

The display 216 may also provide a camera button 1606 for the healthcare provider 210 to select to take a photograph. This may provide an easy method to take the photograph such that the healthcare provider 210 may maintain a steady camera while selecting the camera button 1606 and taking the photograph.

As depicted in the exemplary embodiment in FIG. 16A, the healthcare provider 210 may take the photograph to show the IVC site 204 prior to insertion. This may provide a baseline for measurements that may be used for assessment after the IVC 202 has been inserted. For example, a baseline measurement of lighting, color, skin tone, and hand and arm dimensions may be stored to compare to past and future stored calibrated images. In some embodiments, the calibration zone 1602 is not superimposed on the image 1604 and only an image 1604 of the area prior to insertion of the IVC 202 is photographed. The image 1604 of the IVC site 204 may be stored such that the healthcare provider 210 may visually assess the IVC site 204 and/or the application may compare characteristics of the image 1604 with stored images and historical data. For example, the application may assign a value and a label to the image 1604 associated with the hand color. The image 1604 may also be assigned a value associated with color. In this way, the image 1604 may be taken under different environmental conditions such as, for example, different lighting conditions. The values associated with different conditions may be stored and compared to historical data taken from previous images to normalize the image 1604 by changing the brightness, color, and any other image characteristics such that they may be compared to future images to assess IVC sites for possible complications. This gives a baseline reading prior to insertion of the IVC 202 and allows the healthcare provider 210 to assess the IVC site 204 with future stored calibrated images.

FIG. 16B depicts an exemplary embodiment of the calibration zone 1602 provided by the application on the mobile device display 216. The calibration zone 1602 may be selected from a plurality of calibration zones. In some embodiments, a plurality of calibration zone images may be provided for selection by the healthcare provider 210 or, in some embodiments, the calibration zone 1602 may be selected based on the calibration object or the type of complication. For example, the healthcare provider 210 may assess a color variation associated with the IVC site 204. The healthcare provider 210 may find that calibration of the photograph of the IVC site 204 is easier when a circular bullseye type calibration zone 1602 is used. The healthcare provider 210 may select a bullseye calibration zone 1602 comprising concentric circles of specific diameters such as, for example one millimeter, two millimeters and so on. The two millimeter circle may be matched to the IVC distal hub 203 for image calibration and the photograph taken and the resulting image stored for assessment. In some embodiments, any known dimension of the IVC 202 may be used. The IVC 202 may comprise dimensions set by the International Organization for Standards (ISO) that may be used for calibration.

In some embodiments, the calibration zone 1602 may comprise a circle 1610 and crosshairs 1612 as depicted. The circle 1610 and crosshairs 1612 may be any size and shape including a triangle, rectangle, diamond, star, or any abstract shape that may be beneficial to compare to the calibration object in the image used for calibration. In the embodiment shown, the calibration zone 1602 further comprises four calibration lines 1614, two in opposite directions, projected horizontally from the circle to the sides of the mobile device display 216. Two calibration lines 1616 on the right side of the circle 1610 may be, for example, two millimeters apart. The two calibration lines 1616 on the left side of the circle 1618 may be the same or a different distance apart. The distance of two millimeters is exemplary and, in some embodiments, is used to match the calibration zone 1602 to the standard diameter of the IVC distal hub 203. In some embodiments, the dimension of the distal hub 203 is set by (ISO). Any dimension of the IVC 202, tubes, or any other calibration object with ISO dimensions may be used. It should be understood that any dimension may be used for the distance between the two calibration lines 1516. The distance between the two calibration lines 1616 may be indicative of any known dimension of any calibration object in the image 1604. In the examples described below the calibration object is a catheter and the dimension relates to the catheter distal hub 203 as depicted in FIG. 16 discussed below. The dimension may be changed to any size by the healthcare provider 210 accessing the application. In some embodiments, the healthcare provider 210 may input or select a different calibration object such as, for example, a wrist band width, or tube diameter, and the application may automatically select a dimension. In some embodiments, the healthcare provider 210 may manually input the dimension. In some embodiments, the application may use object recognition to recognize objects in the camera view and calibrate automatically to the recognized objects. Though the IVC 202 is the calibration object that will be discussed in detail herein, the IVC is exemplary and any device with a known dimension may be used to calibrate the image 1604 or any calibrated images discussed below.

Depicted in FIG. 17 is a standard Intravenous Catheter (IVC) which, in some embodiments, is the IVC 202. The diameter at the distal hub 203 is two millimeters. The calibration lines 1616 depicted in FIG. 16B may also be two millimeters such that the healthcare provider 210 may align the calibration lines 1616 with the distal hub 203 to take a calibrated photograph of the IVC site 204 when the IVC 202 is inserted into the patient 200 such that the mobile device 212 is a consistent distance from the IVC site 204 when the calibrated photograph is taken. This allows the healthcare provider 206 and/or the application to assess the site accurately by comparing stored calibrated images.

FIGS. 18 and 19 depict an embodiment in which the patient 200 is receiving the IVC 202 inserted into the patient's cephalic vein at the patient's arm. FIG. 18 presents the healthcare provider 210 inserting the IVC 202 into the arm of the patient 200. FIG. 19 depicts the IVC 202 inserted into the arm and secured such that a calibrated photograph may be taken of the IVC site 204. The IVC 202 is a standard size presenting a two millimeter diameter distal hub 203. The calibration of any images may use the distal hub 203 dimension described in greater detail below.

Depicted in FIG. 20 is an embodiment of a screen provided by the application on the mobile device display 216 including the IVC site 204 in which the IVC 202 is inserted into the cephalic vein of the patient 200. The IVC 202 is inserted into a patient's vein by the healthcare provider 210 and secured with bandages. The IVC 202 is connected to a tube 2002 which supplies the intravenous fluid to the IVC 202. The healthcare provider 210 may move the mobile device 212 such that the calibration zone 1602 is directly over the IVC site 204 and the calibration lines 1514 are aligned with the IVC hub 203. Once the calibration lines 1614 are aligned with the IVC hub 203, the healthcare provider 210 may take the calibrated photograph. In some embodiments, when alignment is achieved, the healthcare provider 210 may take the calibrated photograph by selecting the button 1606 provided on the mobile device display 216 or simply touching the touchscreen display, pressing a button on the side of the device, or by any input that may be available either mechanically or electronically on the mobile device 212. In some embodiments, any peripheral device, or any other method of sensing an input provided by the healthcare provider 210 may be used to take the calibrated photograph or signal the mobile device 212 to take the calibrated photograph. Once the calibrated photograph is taken, the resulting calibrated image 2000 depicting the display presented in FIG. 20 may be stored in the mobile device 212 or the data store 130 and associated with the patient's EMR 214.

The calibrated image 2000 may be normalized using a known color of a calibration object in the calibrated image 2000. For example, the calibration object may be the IVC 202 and the application may measure the color of the IVC 202 and assign a value to the color. The IVC 202 may be used as the calibration object because the IVC 202 is a known manufacturer and the color is known or the application may access a database of known catheters or known colors. When each calibrated image 2000 is taken, there may be different lighting due to, for example, sunlight, different shadows, or the patient 200 may be in a different room. The application may adjust the calibrated image 2000 color and lighting such that the IVC 202 in the calibrated image 2000 matches the color in the previous calibrated images to be compared. This process normalizes the color in the comparative calibrated images. If it is determined that the color of the IVC site 204 in the calibrated image 2000 is different or outside a pre-defined standard error than the color in the baseline or previously taken images, the application may alert the healthcare provider 210 by providing an indication on the mobile device 212 or an alert may be sent to the healthcare provider 210, administration, and/or emergency staff. The application may also analyze the differences between the calibrated images and provide diagnosis and/or possible treatment suggestions.

Turning now to an embodiment of the application presented in FIG. 21, the figure presents an assessment screen 2100 for assessing the calibrated image 2000 of the IVC site 204 where the IVC 202 inserted into the patient's cephalic vein as depicted in FIGS. 17-19. The IVC site 204 assessment screen 2100 may provide the calibrated image 2000 and any information related to the IVC site 204 for selection such as, for example, the dressing condition 2102. A comments field 2104 may also be provided for the healthcare provider 210 to provide any notes.

Turning now to an embodiment of the application presented in FIG. 22 presenting an assessment chart screen 2200, the application displaying the calibrated image 2000 of the IVC site 204 with the IVC 202 inserted into the cephalic vein of the patient 200 and taken by the healthcare provider 210 using the application as described above. Overlaid on the calibrated image 2000 is a measurement chart 2202 for assessing the calibrated image 2000. The healthcare provider 210 may use the measurement chart 2102 to assess the IVC site 204. The measurement chart 2202, as in the example depicted, may provide a swelling observation 2204. For example, the healthcare provider 210 may take a calibrated photograph of the IVC site 204 periodically based on the patient's condition, medication, or any other factor that may require periodic assessment. By comparing the calibrated image 2000 with previously taken calibrated images and using the measurement chart 2202 provided on the mobile device display 216, the healthcare provider 210 may determine the condition of the IVC site 204. For example, the healthcare provider 210 may determine that the patient's arm is swollen. Using the measurement chart 2202, the healthcare provider 210 may provide an indication of the level of swelling at the swelling measurement field 2206 and if the level is above a threshold value the application may provide an alert to the healthcare provider 210, administration, and/or emergency staff. Upon detection of the swelling indication the application may also provide possible diagnosis and/or prompt the healthcare provider 210 to supply more information such as, for example, when the swelling was first noticed, if the patient 200 is in pain, if there is any indication of discoloration with the swelling, or any other symptom that may help deduce a diagnosis. In some embodiments, the application may automatically detect the swelling by comparing the calibrated image 2000 to other calibrated images and present the images along with suggested diagnosis and suggested treatments or actions. In some embodiments, the calibrated image 2000 may also be compared to calibrated images of known complications to determine if and which complication may be present.

Though the measurement chart 2202 is depicted along the side of the assessment chart screen 2200, in some embodiments, the measurement chart 2202 may be overlaid on the calibrated image 2200. Overlaying the measurement chart 2202 on the calibrated image 2200 may make the assessment and measurement of the calibrated image more accurate. Further, the measurement chart 2202 may be moved by selecting the measurement chart 2202 and moving to an area of interest on the calibrated image. In some embodiments, the measurement chart 2202 may be selected from a plurality of measurement charts 2202 that may be displayed as, for example, a ruler, calipers, concentric circles, or any other shape or measurement device that may be digitally displayed on the calibrated image 2000. For example, the healthcare provider 210 may assess a round color variation by selecting the calipers or the concentric circles to determine a radius, diameter, and the coverage area of the color variation. This may provide a more accurate assessment for this particular complication than the exemplary measurement chart 2202 depicted in FIG. 2100.

Further, in some embodiments, the measurement chart 2202 may be used to measure the blood vessel 904 as described above. The measurement chart 2202 may be laid over the calibrated image 2000 and visible blood vessel 904. The measurement chart 2202 may be used to measure the diameter of the blood vessel 904 such that the blood vessel 904 may be analyzed along with the CFD analysis to determine a best vein for the prescribed medicine as discussed above.

In some embodiments, the application may scan the IVC site 204 for different possible signs of complications. FIG. 23 depicts an exemplary color variation observation screen 2300 for indicating color variation observation of the IVC site 204. The color variation observation chart 2302 may indicate the location and coverage of the color variation. The application may use any previously stored images to compare the color or color tone to the calibrated image 2000. The calibrated image 2000 may be normalized using a known color of an object in the calibrated image 2000 as described above. This ensures that the lighting of the room does not affect the color comparison between calibrated images.

In some embodiments, as depicted in FIG. 24, the application may provide a hardness observation screen 2400. The healthcare provider 210 may press on the skin at the IVC site 204 to determine harness of the surrounding skin or on a particular vein to which the IVC 202 is inserted. The hardness chart 2402 may be used to indicate the location and the coverage of the hardness as indicated by the healthcare provider 210. In some embodiments, once the pressure is applied, the calibrated image 2000 is taken for comparison to a baseline hardness image and previous hardness measurements and calibrated images.

FIG. 25 depicts an exemplary assessment summary screen 2500 presented in embodiments of the application where the healthcare provider 210 may review and edit the assessment information. The assessment summary screen 2500 may present patient information 2502, IVC site information 2504, and any observed complication information 2506. The assessment summary screen 2500 may also provide previous calibrated images 2508 along with dates and times such that the healthcare provider 210 may compare the calibrated images 2508. In some embodiments, the healthcare provider 210 may select the calibrated images 2508 for comparison and view the calibrated images 2508 side-by-side or overlaid with the calibrated image 2000. This may assist the healthcare provider 210 in comparing the calibrated images 2508 for any differences that may lead to potential complications.

FIGS. 26-27 depict exemplary complications assessment screen 2600 presented by embodiments of the application in which the healthcare provider 210 has indicated that a new complication is observed. In some embodiments, the application automatically opens the complications assessment screen 2600 when the application compares calibrated images 2508 and determines that there may be a complication with the IVC site 204. The complications assessment screen 2600 may provide the calibrated image 2000 in which it was determined that a complication is present. A complications list 2602 may be displayed that provides a list of complications or observations for selection by the healthcare provider 210. In some embodiments, the application may automatically provide the selected complications list 2602 for verification by the healthcare provider 210.

FIG. 28 depicts a more detailed list of the complication list 2502 presented in FIGS. 26-27. The application may prompt the healthcare provider 210 to input detailed information and a severity score associated with the observed complications. In a first screen 2802 the observed complication 2804 may be selected, in this example, phlebitis. Upon selection of the observed complication 2804 a second window 2806 is opened that provides details about the site observation 2808, a score 2810 associated with the observation, and a stage 2812 of the observed complication 2804 and actions 2814 taken or to be taken. In embodiments, selection of any of the fields may provide hyperlinks, new pages, or scroll menus for selection of fields by the healthcare provider 210. The links may direct the healthcare provider 210 to different screens within the application as presented herein or may connect to services provided by the network or any online pages or websites. Though phlebitis is the exemplary complication discussed herein any possible complications may be determined from a stored list associated with images depicting the complications and indications of the complications such as phlebitis, infection, allergic reaction, compromised dressing, infiltration, and occlusion.

In some embodiments, the application may determine a score 2810 based on the inputs of the previous screens presented in FIGS. 21-27. In some embodiments, the application may determine a score 2810 based on an automatic analysis and comparison of the calibrated images 2508 and, in some embodiments, a comparison of the calibrated images 2508 with a stored history of calibrated images with known complications and associated scores. In any event, the application may send an alert to the healthcare provider 210 or to any emergency staff based on the score 2810, stage 2812, and/or the action 2814.

FIG. 29 depicts an exemplary display screen presented by embodiments of the application for discontinuing the IVC 202 in which complications have been detected automatically by the application comparing the calibrated images 2508 or the healthcare provider indicating through an input that there are complications. The discontinue IVC screen 2900, in some embodiments, presents the calibrated image 2000 that shows the complications that lead to the termination of the IVC dwell. The application may supply a complications list 2902. The complications list 2902 may be a standard list supplied in all cases or may be a suggested list automatically provided by the application based on the analysis of the calibrated image 2000. The discontinue IVC screen 2900 may also present a comments field 2904 for the healthcare provider to provide a description and notes and a time field 2906.

FIG. 30 depicts a discontinued IVC screen 3000 where the application presents a previous IVC site screen 3002 for taking a photograph 3004 of a previous IVC site 3006 once the IVC 202 is removed. The healthcare provider 210 may be prompted for removal of an IVC 202 based on the determined complications. The healthcare provider 210 may select a discontinue previous dwell button via the application interface or the application may automatically direct the healthcare provider 210 to the discontinue IVC screen 3000 when the EMR 214 indicates that the patient 200 is currently connected to the IVC 202. The healthcare provider 210 may utilize a camera of the mobile device 212 to take the photograph 3004 of the previous IVC site 3006. This provides documentation of the location where the IVC 202 was and an image to compare to calibrated images 2508 and store for records and analysis as described in detail below.

FIGS. 31-34, present embodiments of a medication administration screen 3100 for administering various medications via the IVC 202. FIG. 31 presents a screen for providing a selection of intravenous fluids to be administered. FIG. 32 presents a screen providing a schedule for administering continuous and bolus anesthesia drugs. FIG. 33 presents a screen for administration and tracking of patient-controlled analgesics. The embodiments for drug administration, scheduling, and tracking in FIGS. 31-34 are exemplary and any drugs administered to the patient 200 may be recorded and tracked using the application in connection with the patient's EMR 214. The healthcare provider 210 may select any scheduling event by touching the field representing the scheduling event and edit any information in the field selected fields. The application may provide alerts via the mobile device 212 or via the medical facility network based on the information in the medication administration screen.

In some embodiments of the application, the patient 200 may be provided a questionnaire for evaluating the patient's healthcare experience as depicted in the exemplary embodiment in FIG. 35 represented by the questionnaire screen 3500. The information provided by the patient 200 may be automatically stored and evaluated by medical staff and automatically analyzed by the application. The application may store and compare the information supplied by the patient 200 with the information from the IVC assessments as described above. The application may use the compared information to determine likely causes of satisfaction or dissatisfaction of the patient 200. For example, on a scale of 1-5 the patient may indicate that the experience was a 3. The patient may indicate that the score was low because the patient was not satisfied with the skill of the healthcare provider 210. Upon review of a history of feedback information the application may compare all results with similar indications. The application may also determine that multiple insertions were made on multiple occasions. The application determines that multiple insertions relates to lower scores and lower patient satisfaction. The application may also determine that the scores for healthcare provider proficiency has been steadily declining and send a notification to administration relaying the results and the trends and suggest a workshop to re-educate the healthcare staff. The above example may be generalized to any of the Five Rights including Proficiency, Insertion, Vein and Catheter, Supplies and Technology, and Review and Assessment. The patient may be provided questions covering all topics and analysis may be performed relating all questions and patient satisfaction to historical data to determine causes for customer satisfaction. The application may also store and compare any protocol changes and any corrective action and stored dates and times when corrective action is taken and develop trends to determine the effectiveness of the corrective actions.

An exemplary patient discharge screen 3600 to complete the observation and assessment may be provided as depicted in FIG. 36. The healthcare provider 210 may exit the assessment and all information provided by the healthcare provider 210 and the patient 200 is stored and accessible by any person with security clearance to access the information. Upon exit of the assessment, the healthcare provider 210 may also be prompted to input any notes or additional observations and may be provided a questionnaire related to the healthcare provider satisfaction with the assessment and the application.

Upon exit of the assessment, the healthcare provider 210 may also elect to discharge the patient 200 at which point the exemplary patient discharge screen 3600 is presented. The healthcare provider 210 may input the patient information or scan the barcode 206 associated with the patient 200 and enter the reason for discharge. The application may present the healthcare provider 210 with options for selecting a reason for discharge and a discharge field 3602 to receive the reason and a time field 3604. Once the patient 200 is fully discharged the patients EMR 214 may be updated with all information from the patient's stay. The information related to the patient 200 may be added to the stored data for analysis by the system as described in embodiments above.

Turning to an embodiment of a logout screen 3700 depicted in FIG. 37, the healthcare provider 210 may log out of the patient's EMR 214 upon discharge of the patient 200 or when the healthcare provider 210 is assessing a different patient. The healthcare provider 210 may scan the barcode 206 associated with the patient 200 and enter information related to the patient 200. The healthcare provider 210 may select to end rounds or select any link to other screens provided by the application.

FIG. 37 presents an exemplary flow diagram presenting a method 3700 for calibrating IVC site images and assessing the IVC site 204 in embodiments described above. At Step 3702, the healthcare provider 210 accesses the patient's EMR 214 by entering security information and scanning indicia associated with the patient 200 identification number such as the barcode 206 as described in embodiments above. The healthcare provider 210 may also input information into the application via the mobile device 212 indicative of the patient 200. Upon access to the patient information via the patient's EMR 214, the healthcare provider 210 may select to assess the IVC site 204. When the patient 200 is a new patient, the healthcare provider 210 may begin a new patient log in and provide new information related to the patient 200 thus opening a new EMR 214 for the patient 200.

At Step 3704, the calibrated image 2000 of the IVC site 204 may be created by taking a calibrated photograph of the IVC site 204 using the mobile device 212 as described in embodiments above. The healthcare provider 210 may use the mobile device 212 and take a calibrated photograph of the IVC site 204. The healthcare provider 210 may align a calibration zone 1602 with a calibration object, in the embodiments described herein, the IVC 202. The calibration zone 1602 may provide a dimension that may be aligned with a dimension of the calibration object such that each calibrated image 2000 of a plurality of calibrated images 2508 may be similarly aligned with the IVC site 204. This allows the application or the healthcare provider 210 to compare similar calibrated images 2508. In exemplary embodiments described herein, the calibration object is the IVC 202 and the IVC distal hub 203 is used as the dimension for calibration.

At Step 3706, the analysis may be performed on the calibrated image 2000 as described in embodiments above. The calibrated image 2000 may be used to assess the IVC site 204. The healthcare provider 210 may view the calibrated image 2000 and look for any color variation, swelling, hardness, or any other indicator of a complication. The healthcare provider 210 may also assess the IVC site 204 for any dressing issues and make any alterations as needed. In some embodiments, the calibrated image 2000 may be compared to a stored history of calibrated images of the IVC site 204. Comparing the images to previously taken images over time, may allow the healthcare provider 210 to assess any differences in the images and determine possible complications. For example, the healthcare provider 210 may determine, from a comparison of the calibrated images 2508, that the IVC site 204 is swollen. This may be an indicator of complications such as, for example, an infection. The healthcare provider 210 may then take action in response to the complication.

When it is determined that a complication exists, in Step 3708, a comparison of stored images with the same or similar symptoms may be performed to determine the complication as described in embodiments above. The healthcare provider 210 may interview the patient 200 asking questions related to pain, color variation, or any symptoms the patient 200 may be feeling. The interview questions may be provided by the application and a score may be applied upon completion of the interview. The healthcare provider 210 may also compare the calibrated image 2000 with previous calibrated images 2508 and images presenting known complications side-by-side or overlaid on the mobile device 212 to determine the complication and possible diagnosis. In some embodiments, the application automatically compares the calibrated image 2000 and previous calibrated images 2508 as well as images presenting known complications and presents the images as well as suggested diagnosis to the healthcare provider 210. The healthcare provider 210 and/or the application may also determine a score to be associated with the patient 200 and issue an alert if the score is above a threshold value.

At Step 3710, the application may store and compare statistical information related to complications, diagnosis, treatment, and the results to determine the most likely complications and diagnosis and the most successful treatments based on the observations of the IVC site 204. The application may determine the most successful treatment based on the complication or may determine a likelihood of the complication and likelihood of success of treatments. The application may suggest a list with the likelihood of success based on the stored history of success based on the probability of complications. The healthcare provider 210 may select the complication and the treatment from the list and, upon a next assessment, enter a success of treatment or the application may compare future calibrated images to the calibrated image 2000 to determine a success score.

At Step 3712, the application may store information related to the complication, treatment, and success of the treatment. Further, the application may update complication models and treatment models based on information related to the assessment of the IVC site 204. The application may store success trends to determine the likelihood of complications and success as described above. The models may be updated in real-time to use the most current information and the best models. In some embodiments, the calibrated image 2000 may be a video. The healthcare provider 210 may press on the IVC site 204 and take a calibrated video of the process. The calibrated video may then be compared to a baseline video or previous calibrated videos. The comparison may be a visual comparison performed by the healthcare provider 210 or may be automatically performed by the application as described above. Further, the video may be normalized by comparing known objects in the images and adjust any characteristics of individual images to achieve normalized images that may be compared. Any steps provided in embodiments presented above may be mapped to calibrated videos.

FIG. 38 presents an exemplary flow diagram presenting a method 3800 for determining a blood vessel for receiving medication via the IVC. At Step 3802, a doctor determines a diagnosis for the patient and prescribes a medication.

At a Step 3804, blood vessels of the patient are scanned via ultrasonography to determine blood vessel and blood flow characteristics as described in embodiments above. The healthcare provider 210 may use an ultrasound to scan the blood vessel 208 of the patient 200 that may be used for receiving the medication prescribed by the doctor. The blood vessel characteristics may be used to create a model of the blood vessel. In some embodiments, many blood vessels may be imaged and the resulting information stored in the patient's EMR 214. This may be useful to determine the best vessel for medications in the future.

At a Step 3806, the blood vessel characteristics are uploaded into CFD simulation to determine how the medication will interact with the blood vessel 208 and the blood flow as described in embodiments above. The blood pressure, blood temperature, blood flow rate, turbulence, viscosity, medication dispersion, medication dispersion rate, as well as the medication dilution rate may be simulated and stored in the patient's EMR 214. The analysis may be performed on a plurality of blood vessels.

At a Step 3808, the analysis results from a plurality of blood vessels may be compared to determine a best blood vessel for receiving the medication as described in embodiments above. The blood vessels providing satisfactory results may be ranked or given a numerical score related to performance of the blood vessel 904 in dispersing the medication and resisting deterioration. Any blood vessels that are capable of receiving the prescribed dose of medication while maintaining below a threshold of erosion or deterioration may be labeled satisfactory. The blood vessels may be ranked such that, for example, the blood vessel dispersing the medication the fastest while undergoing the least amount of deterioration may be ranked highest.

At a Step 3810, the blood vessels are suggested for receiving the IVC as described in embodiments above. The blood vessels may be recommended based on the resistance to deterioration caused by the medication and the scores as describe above. The blood vessels may also be recommended based on the blood vessel characteristics and medication dispersion in the blood vessel and throughout the body. In some embodiments, the blood vessel and the location on the body for the IVC to be inserted is determined and recommended.

At a Step 3812, the healthcare provider 210 may administer the medication to the suggested blood vessel 904. The healthcare provider 210 may receive instructions for administering the medication along with the medication from the pharmacist or the doctor based on the analysis described above. The healthcare provider 210 may administer the medication into the blood vessel 904 at the location indicated.

In some embodiments, the steps provided in the methods described above may be omitted or rearranged. In some embodiments, steps may be performed by the healthcare provider 210 or by the application. Any method or process that may be performed using any systems as described herein may be added to the methods described above.

In some embodiments, the application is stored on or accessed via a computer, tablet, mobile device, smartphone, and a computer on wheels. The application may be in communication with a device for performing ultrasonography and the application may receive the information obtained from the ultrasonography directly. The information obtained via ultrasonography, the simulation, and the assessment may be stored on the device running the application or at a confidential database associated with the application and/or the patient. In some embodiments, the ultrasonography, simulation, and assessment are run on separate devices and connected communicatively and are associated with the confidential database. In some embodiments, the information from the ultrasonography, the simulation, and the assessment is confidential and not shared with the medical facility or the patient's EMR 214. In some embodiments, the application runs the CFD analysis and the assessment at the device and in some embodiments, the application is a cloud-based application. The information obtained via the ultrasonography, the CFD simulation, and the assessment may be shared to only necessary personnel such as the patient 200 and the healthcare provider 210 as described in embodiments above.

In some embodiments, the ultrasonography information, the CFD analysis, and the assessment results are stored and transmitted using communication protocols such as Digital Imaging and Communication in Medicine (DICOM), Health Level Seven (HL7), Fast Healthcare Interoperability Resources (FHIR), DIRECT, Integrating the Healthcare Enterprise (IHE), and any other healthcare protocol.

In some embodiments, the blood vessel characteristics, blood flow characteristics, simulation results, medication effects, and any other information associated with the modeling and simulation of the blood vessel 904 and the patient 200 may be stored in the EMR 214 of the patient 200 for future use. The IVC site 204 may be periodically assessed and stored in the EMR 214 to update the models as described in embodiments herein.

Although embodiments of this disclosure have been described with reference to the illustrations in the attached drawing figures, it is noted that equivalents may be employed and substitutions made herein without departing from the scope hereof as recited in the claims.

Having thus described various embodiments, what is claimed as new and desired to be protected by Letters Patent includes the following:

1. One or more non-transitory computer-readable media storing computer-executable instructions that, when executed by a processor, perform a method of determining a blood vessel of a patient for receiving a medication via an intravenous catheter, the method comprising the steps of:
   obtaining blood vessel characteristics via ultrasonography;
   generating a blood vessel model based on the blood vessel characteristics;
   simulating blood flow in the blood vessel model;
   simulating an introduction of the medication into the blood vessel model via the intravenous catheter;
   determining a medication effect on the blood vessel model; and
   recommending the blood vessel for receiving the medication based at least in part on the medication effect,
   wherein the medication effect is based at least in part on an effect of the medication flow and the blood flow on the blood vessel model.

2. The method of claim 1, wherein the blood vessel characteristics are indicative of at least a diameter of the blood vessel and are obtained from a calibrated image obtained via a mobile device configured to run the simulation.

3. The method of claim 1, wherein the medication effect comprises at least one of a change in pH and a change in osmolality of a combination of blood and the medication in the blood vessel model.

4. The method of claim 1, wherein the blood flow is simulated using computational fluid dynamics based at least in part on a hemodilution ratio and a size of the blood vessel obtained via ultrasonography.

5. The method of claim 1,
wherein the blood vessel characteristics are received from a peripheral device configured to perform ultrasonography and associated with a mobile device, and
wherein the mobile device is configured to perform an assessment of an intravenous catheter site associated with the intravenous catheter.

6. The method of claim 1, further comprising the steps of:
recommending the blood vessel for receipt of the medication from a plurality of blood vessels and a plurality of simulations; and
recommending at least one infusion rate of the medication,
wherein the recommendation is based at least in part on at least one simulated hemodilution ratio.

7. The method of claim 6, further comprising the steps of:
creating a list of blood vessels sufficient for receipt of the medication from the plurality of blood vessels; and
ranking the plurality of blood vessels based at least in part on a plurality of hemodilution ratios associated with the plurality of blood vessels.

8. The method of claim 7,
wherein the recommended blood vessel and the at least one recommended infusion rate are based at least in part on a determined range of hemodilution ratios, and
wherein the range of hemodilution ratios is based at least in part on a balance between pH and osmolality of a combined blood and medication and the effect on the interior wall of the recommended blood vessel in the simulation.

9. The method of claim 1, further comprising the steps of:
recommending a rate of medication infusion based at least in part on a simulated hemodilution ratio as compared to a stored range of hemodilution ratios;
obtaining an assessment of a site of the intravenous catheter for tracking progress of the patient;
storing the assessment, the blood flow characteristics, the blood vessel model, and the simulation in a confidential database associated with the patient.

10. One or more non-transitory computer-readable media storing computer-executable instructions that, when executed by a processor, perform a method of determining a blood vessel of a patient for receiving a medication via an intravenous catheter, the method comprising the steps of:
obtaining blood vessel characteristics via ultrasonography;
generating a blood vessel model based on the blood vessel characteristics;
simulating blood flow in the blood vessel model;
simulating an introduction of the medication into the blood vessel model via the intravenous catheter;
determining a medication effect on the blood vessel model;
recommending the blood vessel for receiving the intravenous catheter based at least in part on the simulation; and
recommending an infusion rate of the medication into the blood vessel based at least in part on the simulation.

11. The method of claim 10, wherein the ultrasonography is performed via a peripheral device associated with a mobile device, and the mobile device is further configured to assess a site of the intravenous catheter after the medication is injected into the blood vessel.

12. The method of claim 10, wherein the medication effect comprises at least one of a change in pH and a change in dissolved salt in blood in the simulation.

13. The method of claim 10, further comprising the step of comparing the medication effect to an optimal medication effect, wherein the optimal medication effect is determined from experimental data comprising a plurality of medications injected into a plurality of blood vessels.

14. The method of claim 13, further comprising the steps of:
recommending, via a mobile device, a range of medication infusion rates based at least in part on the medication effect,
wherein the medication effect further comprises a range of hemodilution ratios;
assessing, via the mobile device, a site of the intravenous catheter to track progress of the patient after the medication is injected, and
storing, in a confidential database associated with the mobile device, the blood vessel characteristics, the medication effect, and the assessment.

15. One or more non-transitory computer-readable media storing computer-executable instructions that, when executed by a processor, perform a method of determining a blood vessel of a patient for receiving a medication via an intravenous catheter, the method comprising the steps of:
obtaining blood vessel characteristics;
generating a blood vessel model based on the blood vessel characteristics;
simulating blood flow in the blood vessel model;
simulating an introduction of the medication into the blood vessel model via the intravenous catheter;
determining a medication effect on the blood vessel model; and
recommending the blood vessel for receiving the medication based at least in part on the simulation.

16. The method of claim 15, wherein the medication effect comprises at least one of an osmolality and a pH of a combined blood flow and medication and a deterioration of the blood vessel.

17. The method of claim 16, further comprising the step of recommending, to a healthcare provider, the blood vessel from a plurality of blood vessels for receiving the medication based on the medication effect.

18. The method of claim 17, further comprising the steps of:
recommending, to the healthcare provider, a list of blood vessels sufficient for receiving the medication; and
ranking the blood vessels sufficient for receiving the medication based on a range of hemodilution ratios determined from the simulation.

19. The method of claim 18, further comprising the step of recommending an infusion rate of the medication into the blood vessel, wherein the range of hemodilution ratios is based at least in part on blood flow and medication flow in the blood vessel model.

20. The method of claim 19, further comprising the step of assessing a site of the intravenous catheter to track progress of the patient, wherein the assessment, the simulation, the recommendation of the infusion rate of the medication, and the recommendation of the blood vessel is performed via at least one mobile device and stored in a confidential database associated with the patient.

* * * * *